(12) United States Patent
Cafferty et al.

(10) Patent No.: US 9,638,686 B1
(45) Date of Patent: May 2, 2017

(54) ANALYTE SYSTEM AND METHOD FOR DETERMINING HEMOGLOBIN PARAMETERS IN WHOLE BLOOD

(71) Applicant: Nova Biomedical Corporation, Waltham, MA (US)

(72) Inventors: Michael S. Cafferty, Medford, MA (US); Scott P. Cionek, Bolton, MA (US)

(73) Assignee: Nova Biomedical Corporation, Waltham, MA (US)

( * ) Notice: Subject to any disclaimer, the term of this patent is extended or adjusted under 35 U.S.C. 154(b) by 0 days.

(21) Appl. No.: 15/015,278

(22) Filed: Feb. 4, 2016

(51) Int. Cl.
*G01N 33/48* (2006.01)
*G01N 33/49* (2006.01)
*G01N 21/27* (2006.01)
*G01N 33/487* (2006.01)

(52) U.S. Cl.
CPC ......... *G01N 33/492* (2013.01); *G01N 21/274* (2013.01); *G01N 33/48792* (2013.01)

(58) Field of Classification Search
CPC ........... G01N 33/492; G01N 33/48792; G01N 21/274
USPC ......................................................... 356/40
See application file for complete search history.

(56) References Cited

U.S. PATENT DOCUMENTS

| | | | |
|---|---|---|---|
| 4,669,878 A | 6/1987 | Meier | |
| 6,353,471 B1 | 3/2002 | Samsoondar | |
| 2008/0186483 A1* | 8/2008 | Kiesel ................ | A61B 5/14532 356/246 |
| 2010/0240964 A1* | 9/2010 | Sterling ............. | A61B 5/14532 600/300 |
| 2011/0295484 A1* | 12/2011 | L'Henoret ............ | G01N 21/05 701/102 |
| 2016/0178573 A1* | 6/2016 | Sheppard, Jr. ......... | G01N 33/49 356/40 |

* cited by examiner

*Primary Examiner* — Sunghee Y Gray
(74) *Attorney, Agent, or Firm* — Robert R. Deleault, Esq.; Mesmer & Deleault, PLLC

(57) ABSTRACT

A method of measuring whole-blood hemoglobin parameters includes providing a LED light source, guiding light having the spectral range from the LED light source along an optical path, providing a cuvette module with a sample receiving chamber, providing a pair of first and second optical diffusers disposed in the optical path where the cuvette module is disposed between the pair of first and second optical diffusers, guiding light from the cuvette module into an optical spectrometer, and processing an electrical signal from the spectrometer into an output signal useable for displaying and reporting hemoglobin parameter values and/or total bilirubin parameter values of the sample of whole blood.

9 Claims, 13 Drawing Sheets

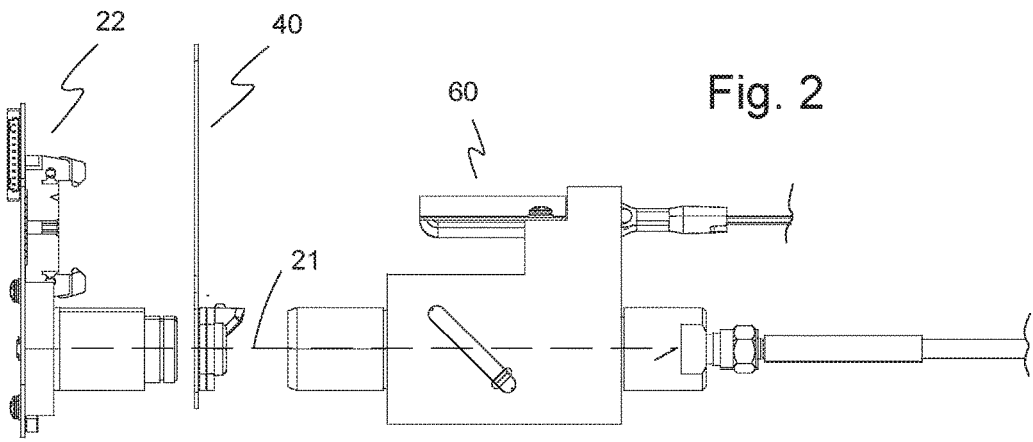
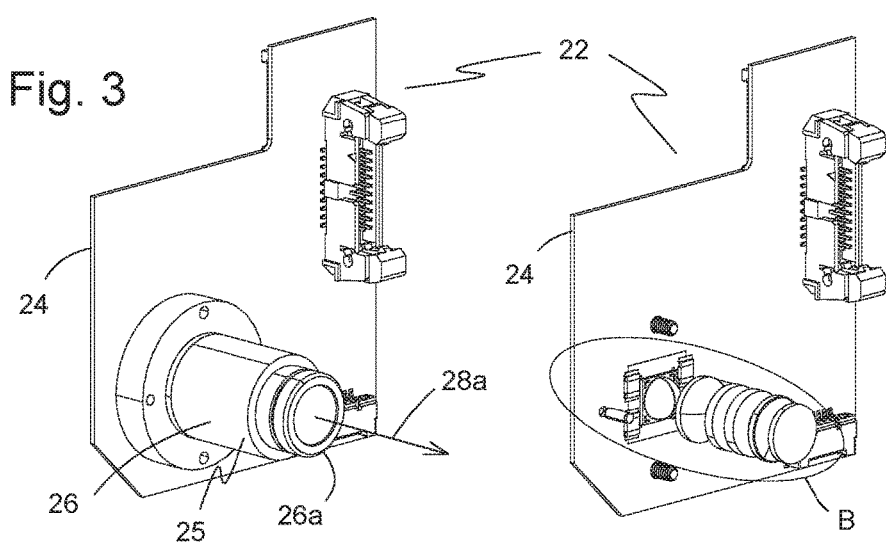
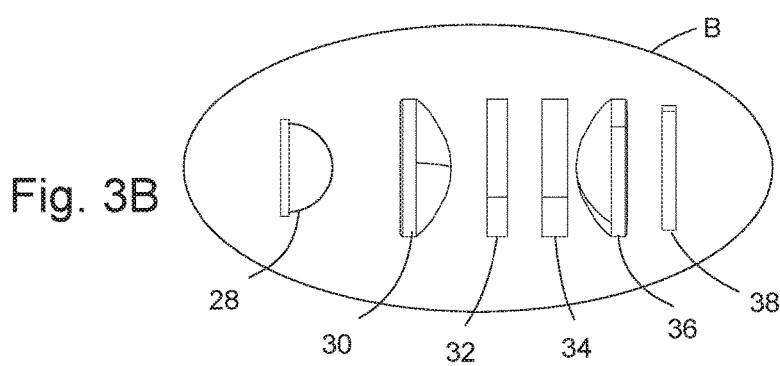

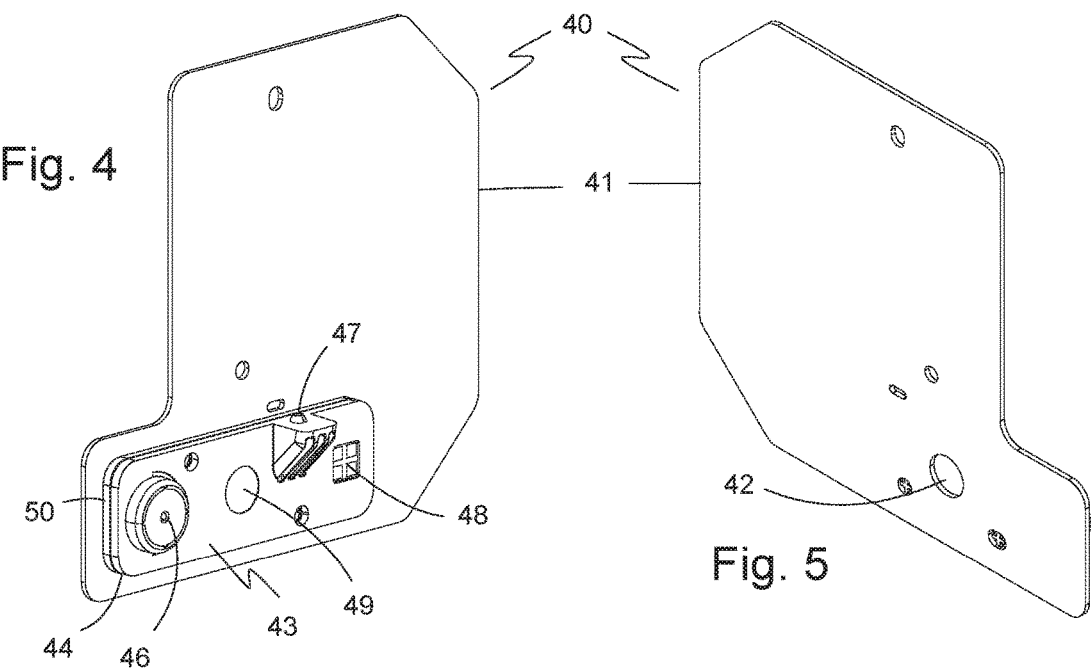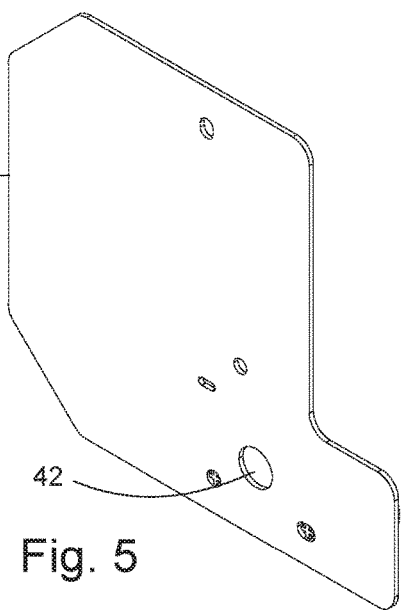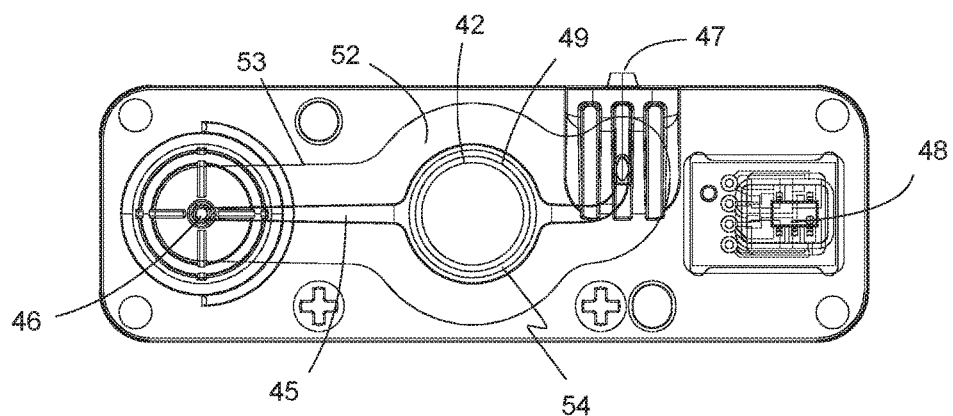

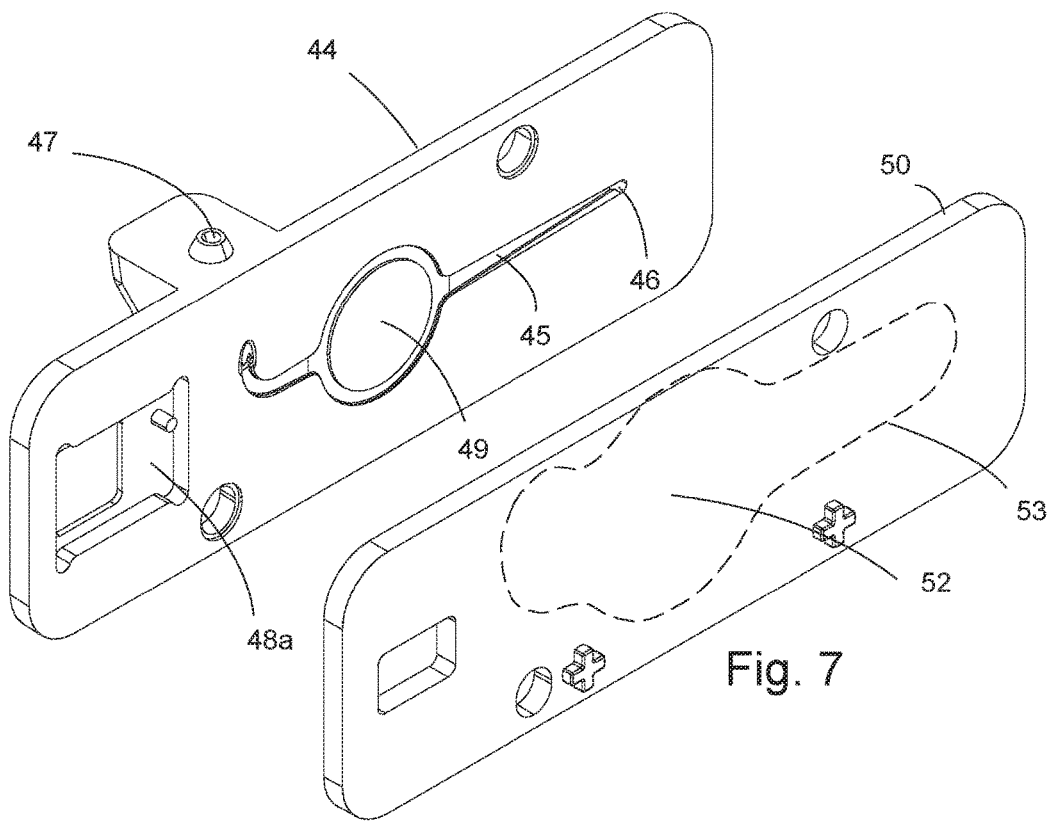
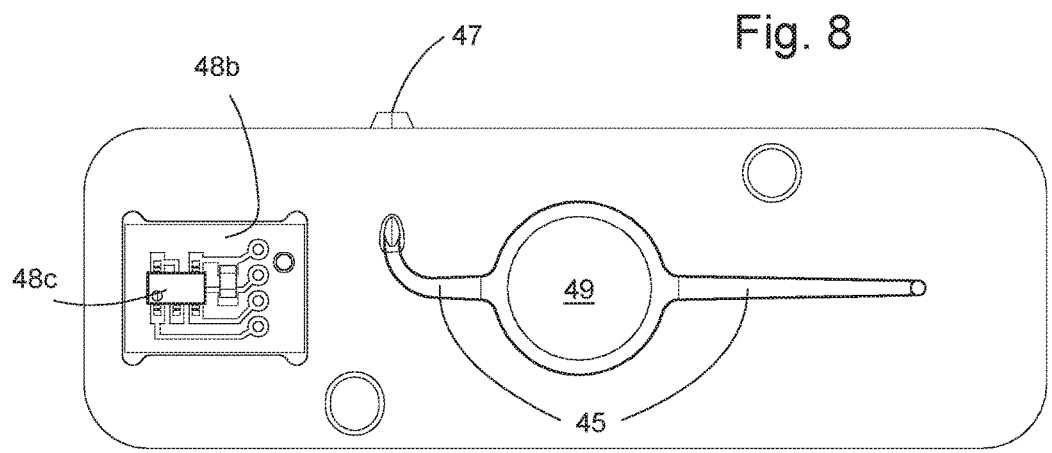

ANALYTE SYSTEM AND METHOD FOR DETERMINING HEMOGLOBIN PARAMETERS IN WHOLE BLOOD

BACKGROUND OF THE INVENTION

1. Field of the Invention

The present invention relates generally to spectroscopic systems and methods for the identification and characterization of hemoglobin parameters in blood.

2. Description of the Prior Art

An ultraviolet-visible light spectroscopic system involves absorption spectroscopy or reflectance spectroscopy. As the name implies, such systems use light in the visible and near ultraviolet ranges for analyzing a sample. The wavelength range is typically from about 400 nm to about 700 nm. The absorption or reflectance of the visible light directly affects the perceived color of the chemicals involved. UV/Vis spectroscopy is routinely used in analytical chemistry for the quantitative determination of different analytes, such as transition metal ions, highly conjugated organic compounds, and biological macromolecules. Spectroscopic analysis is commonly carried out in solutions but solids and gases may also be studied.

A near-infrared spectroscopic system also involves absorption spectroscopy or reflectance spectroscopy. Such systems use light in the near-infrared range for analyzing a sample. The wavelength range is typically from about 700 nm to less than 2,500 nm. Typical applications include pharmaceutical, medical diagnostics (including blood sugar and pulse oximetry), food and agrochemical quality control, and combustion research, as well as research in functional neuroimaging, sports medicine & science, elite sports training, ergonomics, rehabilitation, neonatal research, brain computer interface, urology (bladder contraction), and neurology (neurovascular coupling).

Instrumentation for near-IR (NIR) spectroscopy is similar to instruments for the UV-visible and mid-IR ranges. The basic parts of a spectrophotometer are a light source, a holder for the sample, a diffraction grating in a monochromator or a prism to separate the different wavelengths of light, and a detector. The radiation source is often a Tungsten filament (300-2500 nm), a deuterium arc lamp, which is continuous over the ultraviolet region (190-400 nm), Xenon arc lamp, which is continuous from 160-2,000 nm, or more recently, light emitting diodes (LED) for the visible wavelengths. The detector is typically a photomultiplier tube, a photodiode, a photodiode array or a charge-coupled device (CCD). Single photodiode detectors and photomultiplier tubes are used with scanning monochromators, which filter the light so that only light of a single wavelength reaches the detector at one time. The scanning monochromator moves the diffraction grating to "step-through" each wavelength so that its intensity may be measured as a function of wavelength. Fixed monochromators are used with CCDs and photodiode arrays. As both of these devices consist of many detectors grouped into one or two dimensional arrays, they are able to collect light of different wavelengths on different pixels or groups of pixels simultaneously. Common incandescent or quartz halogen light bulbs are most often used as broadband sources of near-infrared radiation for analytical applications. Light-emitting diodes (LEDs) are also used. The type of detector used depends primarily on the range of wavelengths to be measured.

The primary application of NIR spectroscopy to the human body uses the fact that the transmission and absorption of NIR light in human body tissues contains information about hemoglobin concentration changes. By employing several wavelengths and time resolved (frequency or time domain) method and/or spatially resolved methods, blood flow, volume and absolute tissue saturation ($StO_2$ or Tissue Saturation Index (TSI)) can be quantified. Applications of oximetry by NIRS methods include neuroscience, ergonomics, rehabilitation, brain computer interface, urology, the detection of illnesses that affect the blood circulation (e.g., peripheral vascular disease), the detection and assessment of breast tumors, and the optimization of training in sports medicine.

With respect to absorption spectroscopy, the Beer-Lambert law states that the absorbance of a solution is directly proportional to the concentration of the absorbing species in the solution and the path length. Thus, for a fixed path length, UV/Vis and NIR spectroscopy can be used to determine the concentration of the absorber in a solution. The method is most often used in a quantitative way to determine concentrations of an absorbing species in solution, using the Beer-Lambert law:

$$A = \log_{10}(I_0/I) = \epsilon c L$$

where A is the measured absorbance, in Absorbance Units (AU), $I_0$ is the intensity of the incident light at a given wavelength, I is the transmitted intensity, L the path length through the sample, and c the concentration of the absorbing species.

For each species and wavelength, $\epsilon$ is a constant known as the molar absorptivity or extinction coefficient. This constant is a fundamental molecular property in a given solvent, at a particular temperature and pressure, and has units of 1/M*cm or often AU/M*cm. The absorbance and extinction $\epsilon$ are sometimes defined in terms of the natural logarithm instead of the base-10 logarithm.

The Beer-Lambert Law is useful for characterizing many compounds but does not hold as a universal relationship for the concentration and absorption of all substances.

It is recognized by those skilled in the art that various factors affect these spectroscopic systems. These factors include spectral bandwidth, wavelength error, stray light, deviations from the Beer-Lambert law, and measurement uncertainty sources.

Stray light is an important factor that affects spectroscopic systems. Stray light causes an instrument to report an incorrectly low absorbance.

Deviations from the Beer-Lambert law arise based on concentrations. At sufficiently high concentrations, the absorption bands will saturate and show absorption flattening. The absorption peak appears to flatten because close to 100% of the light is already being absorbed. The concentration at which this occurs depends on the particular compound being measured.

Measurement uncertainty arises in quantitative chemical analysis where the results are additionally affected by uncertainty sources from the nature of the compounds and/or solutions that are measured. These include spectral interferences caused by absorption band overlap, fading of the color of the absorbing species (caused by decomposition or reaction) and possible composition mismatch between the sample and the calibration solution.

SUMMARY OF THE INVENTION

It is known that human hemoglobin (HGB) is an oxygen carrying protein in erythrocytes. The determination of its concentration in whole blood is a useful and important diagnostic tool in clinical biochemistry. COOx analyzers are used to measure the hemoglobin parameters of blood, such as total hemoglobin (tHb), carboxyhemoglobin (COHb), deoxyhemoglobin (HHb), oxyhemoglobin (O2Hb), methemoglobin (MetHb), and fetal hemoglobin (FHb) as well as total bilirubin (tBil) using optical absorbance measurements. In practice, typical COOx analyzers use lysed blood instead of whole blood because of the problems encountered with spectrometric analysis of whole blood. The measurement of lysed blood is relatively straightforward since the lysing process dissolves the red blood cells and turns the blood into an almost non-diffusing medium. The absorbance is measured with a simple collimated beam through the cuvette with little loss of light due to scattering. Because of the low loss of light due to scattering, a straightforward linear analysis may be used to find the hemoglobin and total bilirubin parameters.

Measurement of hemoglobin and total bilirubin parameters using a whole blood sample is very challenging due to the strong optical scattering of whole blood. These problems are primarily related to handling the increased light scattering level of whole blood as compared to lysed blood. This introduces light loss and nonlinear absorbance into the measurement.

The components in a prism-based spectrometer naturally have a low stray light profile. The major contributing factor to stray light performance is related to how the components are used.

Although the problems are primarily related to handling the increase light scattering level of whole blood, it is not a single factor that, if resolved, is capable of solving these difficult problems. The inventors have identified several factors that need to be addressed in order to measure hemoglobin parameters in whole blood. Because whole blood is a very diffuse medium, it is necessary to collect as much light as possible to reduce the requirement for an upper absorbance measurement range. It is also necessary to expand the upper limit of the measured absorbance due to the lower range of detector linearity correction. Blood settling effects are another problem that leads to poor correlation of absorbance of whole blood scans to absorbance of lysed blood scans. Basically, the blood cells are forming clumps or rouleaux. LED white light source brightness must also be increased. Lastly, new algorithms other than linear-based algorithms are needed to overcome the light scattering effects of whole blood.

Typical collection optics for systems using lysed blood are designed to collect light from the cuvette in a cone of about +/−0.7 degrees wide and have an upper measure absorbance limit of 1.5 A.U. (absorbance units). It was discovered by the inventors that for whole blood the system needs to collect light from the cuvette in a cone of about +/−12 degrees and that the upper absorbance limit had to increase to about 3.5 A.U. As for blood settling effects, the typical time it takes to measure the absorbance spectrum (approx. 1 minute), the whole blood in the cuvette is settling and the blood cells are forming clumps or rouleaux. Consequently, the scattering effects and the absorbance change with time. The inventors discovered that changing the spectrometer control to collect multiple scans frequently rather than a few scans averaged over a longer period avoided step functions in the composite absorbance scan, which is stitched together from scans from several integration times. Unfortunately, adding more scans to expand the absorbance upper limit increases the data collection time. To resolve this dilemma, integration time was lowered from 5 msec to 1.2 msec to reduce data collection time. It was discovered, however, that this only works if the light level is increased by a corresponding factor. Thus, the LED white light brightness must be increased.

The optical absorbance measurement of a diffuse sample such as whole blood presents a unique problem. The diffuse transmittance of the whole blood sample scrambles the initial spatial light distribution of the measurement system caused by the non-uniformity typical of light sources. Thus, the spatial light distribution of the "blank" scan can be quite different from the whole blood sample scan. Since optical detectors have response that varies spatially, the response can vary due to spatial distribution changes of the incident light, even if the overall intensity has not changed. An absorbance scan which is based on the ratio of the whole blood sample scan to the blank scan will have a significant absorbance component due to this non-uniformity of the light source in addition to the absorbance due to the sample alone. This results in a significant measurement error of the whole blood sample absorbance that is intolerable for cooximetry.

It was discovered that, by placing the sample cuvette between diffusers, the spatial light distribution appears the same for the blank and sample scans, thus, removing this error effect. The diffusers are specially chosen so that they diffuse a ray of incident light into the full acceptance cone of the optical system, but not more, so that as much light throughput as possible may be preserved while scrambling the ray completely across the field.

In addition, the measurement of fetal hemoglobin parameters presents additional problems. These include spectral acquisition times, which must be faster. Instead of the typical 12 seconds, it must be 5 seconds or less. The spectral acquisition time includes integration time multiplied by the number of co-added spectra and the processing time to produce one spectrum (full light, dark or sample) meeting all the following requirements. Absolute wavelength accuracy must be less; less than +0.03/−0.03 nm compared to +0.1/−0.0 nm. Wavelength calibration maintenance (less than +0.06/−0.0 nm versus +0.1/−0.0 nm), wavelength calibration drift (less than 0.024 nm/° C. compared to 0.04 nm/° C.), dark current level (less than 0.06%/° C. for maximum dynamic range versus 0.1%/° C. of maximum dynamic range), response nonlinearity (less than 0.06% after correction and less than 1.2% for lowest and highest 10% of dynamic range compared to 0.1% after correction and 2.0% for lowest and highest 10% of dynamic range), scattered light level (less than 0.02% of maximum dynamic range for fully illuminated detector array versus 0.1% of maximum dynamic range for fully illuminated detector array), thermal drift of response (intensity change maximum of 6% and tilt max of 6% over spectral range compared to intensity change maximum of 10% and tilt max of 10% over spectral range), and temperature excursion allowed during measurement (less than 0.5° C. compared to 2° C.) must all be less. The present invention includes these additional features for use in measuring fetal hemoglobin parameters.

In another aspect of the present invention, commercially available compact and low-cost spectrometers typically use diffraction gratings (reflective or transmissive) to disperse the light input. Diffraction gratings give a high degree of dispersion in a small volume, and produce a relatively constant bandwidth (or resolution) vs. wavelength preferred by the typical user. Gratings, however, suffer from high stray light due to multiple diffraction orders and also from the imperfections inherent in the lines that are etched to produce the grating surface. Thus, mass-produced but expensive master holographic gratings are typically employed in applications requiring low stray light, rather than the more commonly available replicated gratings.

The requirement for low stray light for COOx analyzers limits the population of suitable grating manufacturers to the several in the world that produce master holographic or individually precision photoetched gratings. This serves to make it difficult to get low-cost high-performance gratings in quantity.

Prisms are also used to make spectrometers. Prisms have no issues with multiple diffraction orders and their surfaces have orders of magnitude fewer imperfections than the surface of a grating. The components in a prism-based spectrometer naturally have a low stray light profile. Thus, stray light in a prism spectrometer can potentially be lower by an order of magnitude or more compared to a grating spectrometer of otherwise similar design. The major contributing factor to stray light performance arises from how the components are used. There are three main sources of stray light. These include (1) overfilling of the spectrometer numerical aperture, (2) retroreflection from the light-array detector, and (3) the focal plane image. Light in excess of that required to fully illuminate the numerical aperture of the spectrometer can bounce around in the spectrometer and land on the detector. In the present invention, the numerical aperture of the optical fiber is 0.22 and the numerical aperture of the prism spectrometer is 0.1. A stop placed above the optical fiber input restricts the light input cone from the optical fiber to prevent excess light input. The light-array detector does not absorb all of the light impinging upon it, but back-reflects a portion. This retroreflection must be controlled to land into an absorbing surface or beam trap to prevent it from scattering onto the detector. Imparting a slight tilt of the light-array detector forces the retroreflection back into a harmless direction. The image of the slit on the detector focal plane must be as sharp as possible. Any excessive overfill of the detector due to defocus can be a potential source of stray light. If this light hits detector structures such as bond wires, metallization pads, etc., it can bounce back onto the sensitive surface of the detector.

Additionally, a prism spectrometer spreads the blue end of the spectrum out over more pixels than a diffraction grating spectrometer and, thus, the blue end of the spectrum gives a lower signal per pixel. To compensate for the lower signal per pixel, an LED with higher blue power, or a cool-white LED, is used. The signal in the blue can be further boosted by adding an inexpensive filter glass after the LED that slightly attenuates the red end. Kopp filter glass type 4309, about 3 mm thick, is useful for this purpose. The main disadvantage of prisms is the lower dispersive power they have compared to a grating, and the variation of resolution with wavelength. In the present invention when a prism is used, the former disadvantage is mitigated by using a small enough light-array detector; the latter is mitigated because the analysis of whole blood does not require a uniformly small resolution across the waveband of interest.

Currently available spectrometers typically list a uniform 1 nm resolution for the blood measurement spectral region of 455-660 nm. In the present invention, the spectral region is expanded and covers the spectral region of 422-695 mm. Further, the resolution is selectively changed upward in regions where low resolution is not required (such as the 600-695 nm region and 422-455 nm region). In the present invention, these regions have a resolution greater than 1 nm. Typically, the resolution is about 3.0 to about 3.5 nm. These ranges are used to capture additional wavelength calibration peaks for wavelength calibration and fluid detection. The larger spectral region of the present invention requires consideration of the dispersed spectrum from the prism. The dispersed spectrum must be spread out over the light-array detector and cover enough pixels to sample the spectrum at a fine enough resolution but not so much as to extend outside of the detector array. Due to the wider spectral range, the present invention incorporates a light-array detector having 1024 pixels with an active area length of about 8.0 mm.

A minimal-part reference design for an optical dispersion spectrometer requires only two optical components: a light dispersion element (i.e. prism or grating) and a doublet (achromatic) lens. The prism/grating has a reflective coating on the base. One example of an acceptable prism is a Littrow prism. The Littrow prism has a structure such that it is usable for a compact and low-cost spectrometer of the present invention. The prism material (dispersion characteristic) and the lens focal length are further considerations. Although other prisms and achromatic lenses may be used, one embodiment of the present invention incorporates a Schott F5 glass prism and an 80 mm focal length lens. This particular combination provides a dispersion length of the spectrum of about 6.48 mm. This dispersion length leaves about 0.75 mm on either end of the light-array detector available for tolerance variations and dark correction pixels.

Thermal drift of the spectral response must be considered. It is critical that the spectral response of the spectrometer stays within a certain range between the full light and whole blood scans. Any change in spectrometer response will cause absorbance errors. The main precaution against this change is to make sure that the image of the slit overfills the pixels so that image drift due to temperature does not cause a reduction of light on the detector pixel. The 1:1 imaging of the system combined with a 200 μm diameter optical fiber overfills the 125 μm tall pixels. As long as image drift is confined to less than about 30 μm of movement in either direction along the detector over a measurement interval, thermal drift is not a problem. The present invention also contemplates various mechanisms to minimize thermal drift effects on the spectral response. These mechanisms include insulating the spectrometer housing to minimize temperature changes external to the spectrometer housing, maintaining the temperature within the spectrometer housing using a temperature-controlled heat source, and/or incorporating a temperature-compensating lens mount for the achromatic lens.

The process of the present invention that transforms the electrical signals from the spectrometer will now be discussed. First, the absorbance is measured, which is minus the base-ten logarithm of the ratio of the electrical signal received when the blood sample is in the cuvette to the electrical signal received when a clear fluid is in the cuvette. Second, the absorbance values at each wavelength are put into a mapping function that maps absorbance values to the analyte levels (COOx parameters and bilirubin) in the whole blood sample. The mapping function and its coefficients are established by using the absorbance values measured for whole blood samples with known analyte values, and establishing the relationship between these absorbance values and the known analyte values.

The present invention achieves these and other objectives by providing a compact, low-cost COOx analyzer subsystem.

In one embodiment of the present invention, there is a system for measuring whole-blood hemoglobin parameters that includes (a) an optical-sample module having a light-emitting module, a replaceable cuvette assembly, and a calibrating-light module, (b) an optical fiber, (c) a spectrometer module, and (d) a processor module. The light-emitting module has an LED light source capable of emitting light where the light is directed along an optical path. The cuvette assembly is adjacent the light-emitting module where the cuvette assembly is adapted for receiving a whole-blood sample and has a sample receiving chamber with a first cuvette window and a second cuvette window aligned with each other. The sample receiving chamber is disposed in the optical path for receiving light from the LED light source and has a defined optical path length between the first cuvette window and the second cuvette window along with an electronic chip capable of storing a path-length value of the sample receiving chamber. The calibrating-light module has a calibrating-light source with one or more known wavelengths of light where the calibrating-light module is capable of emitting a calibrating light into the optical path. The optical fiber has a light-receiving end and a light-emitting end. The light-receiving end optically connects to the optical-sample module where the light-receiving end receives the light from the optical path and conducts the light to the light-emitting end. The spectrometer module receives the light from the light-emitting end of the optical fiber, separates the light into a plurality of light beams where each light beam has a different wavelength, and converts the plurality of light beams into an electrical signal. The processor module (1) obtains the path-length value of the sample receiving chamber of the replaceable cuvette from the electronic chip and (2) receives and processes the electrical signal from the spectrometer module generated for a whole-blood sample. The path-length value of the sample chamber is used to transform the electrical signal into an output signal useable for displaying and reporting hemoglobin parameter values and/or total bilirubin parameter values for the whole-blood sample.

In another embodiment of the present invention, the light-emitting module includes a plurality of optical components disposed in the optical path between the LED light source and the cuvette assembly where the plurality of optical components includes at least an optical diffuser and one or more of a collimating lens, a circular polarizer, and a focusing lens.

In a further embodiment of the present invention, the calibrating-light module includes a diffuser disposed in the optical path downstream from the cuvette assembly but upstream from a beam splitter.

In still another aspect of the present invention, there is disclosed an optical absorbance measurement system for whole blood. The system includes an optical-sample module, an optical fiber, a spectrometer module, and a processor module. The optical-sample module includes a light-emitting module, a cuvette module, a first optical diffuser, and a second optical diffuser. The cuvette module is positioned between the first optical diffuser and the second optical diffuser. The spectrometer module receives the light from the light-emitting end of the optical fiber, separating the light into a plurality of light beams and converting the plurality of light beams into an electrical signal. The processor module receives and processes the electrical signal from the spectrometer module generated for the whole-blood sample and transforms the electrical signal into an output signal useable for displaying and reporting hemoglobin parameter values and/or total bilirubin parameter values for the whole-blood sample.

In yet another embodiment, the spectrometer module includes an input slit positioned in the optical path to receive the light emitted from the light-emitting end of the optical fiber and to transmit the light therethrough, a light dispersing element disposed in the optical path where the light dispersing element receives the light transmitted through the input slit, separates the light into the plurality of light beams where each light beam has a different wavelength, and re-directs the plurality of light beams back toward but offset from the input slit, and a light-array detector capable of receiving the plurality of light beams and converting the plurality of light beams into an electrical signal for further processing.

In another embodiment, the spectrometer module has a thermal-compensating means for maintaining a position of the plurality of light beams on the light-array detector. The thermal-compensating means includes one or more of insulation disposed around the spectrometer housing, a temperature controller assembly disposed on the spectrometer housing (the temperature controller assembly being, for example, a heating tape with a thermistor or other temperature measuring component and a program that controls the heating of the tape based on the temperature within the spectrometer housing), and a thermal-compensating lens mount.

In a further embodiment, the thermal-compensating lens mount has a fixed mount end and an unfixed mount end that permits thermal expansion and contraction of the thermal-compensating lens mount. The fixed mount end is fixedly attached to a baseplate or a bottom of the spectrometer housing. The lens mount has a coefficient of expansion greater than the coefficient of expansion of the baseplate or the spectrometer housing to which the lens mount is attached. The thermal-compensating lens mount moves linearly and transversely relative to an optical path of the light from the light input slit based on the coefficient of expansion of the lens mount. This temperature-based movement of the lens mount maintains the position of the dispersed light from the light dispersing element onto the light-array detector. In other words, thermal re-positioning of the achromatic lens by way of the thermal-compensating lens mount causes the dispersed light from the light dispersing element to impinge onto the light-array detector without affecting the electric signal generated by the light-array detector from the impinging light. The shift of the light beam is caused by the light-dispersing element reacting to a temperature change.

In another embodiment, there is disclosed a compact spectrometer for measuring hemoglobin parameters in whole blood. The spectrometer includes an enclosed housing having a light input end/an optical fiber housing end with a light entrance port, a light input slit disposed on an electronic circuit substrate, the electronic circuit substrate disposed in the enclosed housing where the light input slit is aligned with and adjacent to the light entrance port, a light-array detector disposed on the circuit board substrate adjacent the light input slit, and an optical component group consisting of a light dispersing element disposed downstream from the light input slit and a spherical achromatic lens disposed between the light input slit and the light dispersing element where the light dispersing element has a reflective surface on a back side to reflect the dispersed light back toward the achromatic lens. The achromatic lens transmits light from the light input slit to the light dispersing element and transmits dispersed light reflected from the light dispersing element to the light-array detector. To accomplish this, the achromatic lens is slightly off axis relative to the light coming from the light input slit so that the dispersed light from the light dispersing element is not directed back to the light input slit but to the light-array detector.

In a further embodiment, there is disclosed a method of measuring whole-blood hemoglobin parameters despite strong optical scattering caused by whole blood. The method includes providing a light source such as a LED light source with a spectral range of about 422 nm to about 695 nm, guiding light having the spectral range from the light source along an optical path, providing a cuvette module with a sample receiving chamber having a first cuvette window disposed in the optical path where the first cuvette window transmits the light through the sample receiving chamber and through a second cuvette window aligned with the first cuvette window where the sample receiving chamber contains a sample of whole blood, providing a pair of diffusers (i.e. a first diffuser and a second diffuser) disposed in the optical path where the first cuvette window and the second cuvette window of the sample receiving chamber of the cuvette are disposed between the pair of diffusers, guiding light from the cuvette module into a spectrometer having a light dispersing element that separates the light into a plurality of light beams where each light beam has a different wavelength and converts the plurality of light beams into an electrical signal, and processing the electrical signal into an output signal useable for displaying and reporting hemoglobin parameter values and/or total bilirubin parameter values of the sample of whole blood.

In another embodiment of the method, the processing step includes processing the electrical signal to spectral absorbance and then mapping the spectral absorbance to hemoglobin parameter values and/or bilirubin parameter values using a computational mapping function.

In still another embodiment of the method, the processing step includes using a kernel-based orthogonal projection to latent structures mapping function as the computational mapping function.

In another embodiment of the method, there is disclosed a method of measuring hemoglobin parameters in a whole blood sample. The method includes (1) measuring and recording a transmitted light intensity scan over a plurality of wavelengths in a measurement range by transmitting light through a cuvette module having an optical path with a known optical path length therethrough where the cuvette module is filled with a transparent fluid, (2) measuring and recording a transmitted light intensity scan over the plurality of wavelengths of the measurement range by transmitting light through the cuvette a second time having the optical path with the known optical path length therethrough where the cuvette module is filled with a whole blood sample, wherein each measuring and recording step of the transparent fluid and the whole blood sample includes diffusing and circularly polarizing the transmitted light before transmitting the transmitted light through the cuvette module and then diffusing the transmitted light emitting from the cuvette module before determining a spectral absorbance, (3) determining a spectral absorbance at each wavelength of the plurality of wavelengths of the measurement range based on a ratio of the transmitted light intensity scan of the whole blood sample to the transmitted light intensity scan of the transparent fluid using a prism-based spectrometer, and (4) correlating the absorbance at each wavelength of the plurality of wavelengths of the measurement range to hemoglobin parameter values and/or bilirubin parameter values of the blood sample using a computational mapping function.

BRIEF DESCRIPTION OF THE DRAWINGS

FIG. 2 is a side elevation view of one embodiment of an optical-sample module shown in FIG. 1.

FIG. 3 is a front, perspective view of one embodiment of a light-emitting module of the optical-sample module shown in FIG. 2.

FIG. 3A is a front, perspective view of the light-emitting module shown in FIG. 3 showing a plurality of optical components.

FIG. 3B is an enlarged, side elevation view of the optical components shown in FIG. 3A.

FIG. 4 is a front perspective view of one embodiment of a cuvette assembly of the optical-sample module shown in FIG. 1.

FIG. 5 is a rear perspective view of the cuvette assembly shown in FIG. 4.

FIG. 6 is a front elevation view of a cuvette module of the cuvette assembly showing fluid input and output ports, a sample receiving chamber, a sample window, and an electronic chip assembly.

FIG. 7 is a rear perspective view of the sample receiving chamber of FIG. 6 showing cuvette first and second windows.

FIG. 8 is a rear plan view of the sample receiving chamber showing the electronic chip assembly disposed adjacent the sample receiving chamber.

DETAILED DESCRIPTION

Figure 1:
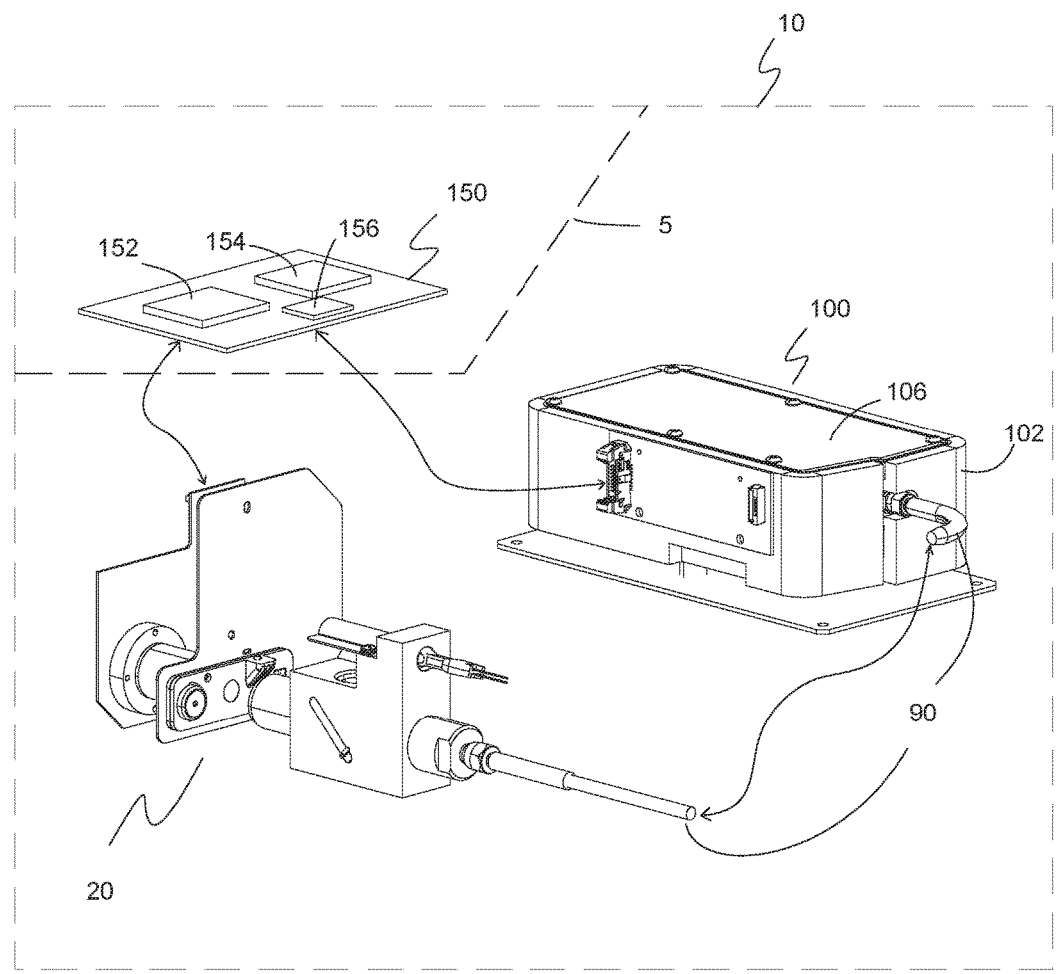
FIG. 1 is a simplified, perspective view of one embodiment of the present invention showing a compact COOx subsystem.

Embodiments of the present invention are illustrated in FIGS. 1-24. FIG. 1 shows one embodiment of a COOx analyzer subsystem 10. COOx analyzer subsystem 10 includes at least an optical-sample module 20, an optical fiber 90 and a spectrometer module 100. COOx analyzer subsystem 10 may optionally include a processor module 150 or processor module 150 may optionally be included in an electronics circuit of a diagnostic system in which the COOx analyzer subsystem 10 is a part. Line 5 is included to signify that the processor module 150 may or may not be part of the COOx subsystem 10. Processor module 150 includes, but is not limited to a microprocessor module 152 and a memory module 154. Optionally, the processor module 150 may also include a converter module 156 or converter module 156 may be external to the COOx analyzer subsystem 10. COOx analyzer subsystem 10 is used to measure the hemoglobin parameters of blood such as total hemoglobin (tHb), carboxyhemoglobin (COHb), deoxyhemoglobin (HHb), oxyhemoglobin (O2Hb), methemoglobin (MetHb), and fetal hemoglobin (FHb) as well as total bilirubin (tBil) using optical absorbance.

FIG. 2 illustrates optical-sample module 20. Optical-sample module 20 includes a light-emitting module 22, a cuvette assembly 40 and a calibrating-light module 60. Light-emitting module 22, as the term implies, emits a visible light beam toward the cuvette assembly 40 that is then received by the calibrating-light module 60, which is then transmitted to spectrometer module 100. The light beam 12 defines an optical path 21.

FIGS. 3-3A illustrate perspective views of the embodiment of light-emitting module 22 of FIG. 2. Light-emitting module 22 includes a light-emitting module substrate 24 that contains an electrical circuit (not shown) and a light-emitting optics assembly 25. Light-emitting optics assembly 25 has an optics assembly housing 26 with an optics assembly end 26a. A beam of visible light 28a emits from optics assembly end 26a of light-emitting optics assembly 25 when light-emitting module 22 is powered on by a signal received from processor module 150. FIG. 3A illustrates light-emitting optics assembly 25 with optics assembly housing 26 removed exposing a plurality of optical components B contained within light-emitting assembly 25.

Turning now to FIG. 3B, there is illustrated an enlarged side view of the plurality of optical components B of FIG. 3A. In this embodiment, optical components B includes a light-emitting diode (LED) light source 28, a collimating lens 30, a first diffuser 32, a circular polarizer 34, a focusing lens 36, and an optional protective window 38. Circular polarizer 34 provides a distinct advantage. This advantage provides improved sensitivity and accuracy of the system. Hemoglobin has optical rotary characteristics, which means that the polarization sensitivity of a spectrometer will cause an absorbance error if non-circularly polarized light is used to measure hemoglobin absorbance. Unlike for other polarization states of light, the polarization state of the circularly polarized light is not changed when passing through hemoglobin. Thus, the polarization response of the spectrometer is the same for the circularly polarized light passing through the hemoglobin as it is for the reference scan taken with the cuvette filled with a transparent fluid.

FIGS. 4 and 5 illustrated front and rear perspective views of one embodiment of the cuvette assembly 40. Cuvette assembly 40 includes a cuvette substrate 41 and a cuvette module 43. Cuvette substrate 41 provides a support for securing the cuvette assembly 40 within the analyte subsystem 10 and includes a cuvette light path opening 42 that is disposed within optical path 21 and is aligned with the light beam emitted from light-emitting module 22. Cuvette module 43 includes a cuvette first portion 44 having a sample receiving recess 45, a sample inlet port 46, a sample outlet port 47, an electronic chip assembly 48, and a first cuvette window 49, and a cuvette second portion 50 having a second cuvette window 52 (shown in FIG. 6 and delineated as outline 53) opposite and aligned with the first cuvette window 49 where the first and second cuvette windows 49, 52 are aligned with and dispersed within optical path 21. Cuvette first portion 44 and cuvette second portion 50 are bonded to each with or without a gasket disposed between cuvette first and second portions 44, 50. Bonding may be achieved using adhesives, ultrasonic techniques, solvent based techniques, etc. When assembled and as shown in FIG. 6, sample receiving recess 45 of cuvette first portion 44 forms a sample receiving chamber 54 with cuvette second portion 50 that fluidly communicates with sample inlet and outlet ports 46, 47. The distance between first and second cuvette windows 49, 52 of sample receiving chamber 54 define a cuvette optical path length, which is accurately measured and stored within electronic chip 48 for later retrieval by processor module 150. A typical optical path length used in this embodiment of the present invention is 0.0035 inches (0.090 mm).

Turning now to FIG. 7, there is illustrates an enlarged, rear perspective view of cuvette first and second portions 44, 50. As shown, cuvette first portion 44 has sample chamber recess 45 with first cuvette window 49 and electronic chip recess 48a for receiving electronic chip assembly 48. Cuvette second portion 50 has second cuvette window 52 that forms sample receiving chamber 54 when assembled together with cuvette first portion 44. Second cuvette window 52 as delineated by an outline 53 on cuvette second portion 50 is a raised surface that forms a water-tight seal around sample chamber recess 45 and sample receiving chamber 54. Optionally, a thin gasket may be positioned between cuvette first and second portions 44, 50 to more easily ensure a water-tight seal. FIG. 8 shows a rear view of cuvette first portion 44 with electronic chip assembly 48 disposed within electronic chip recess 48a. Electronic chip assembly 48 includes a chip circuit board 48b and an electronic chip 48c that stores the cuvette optical path length value for the particular cuvette module 43. First cuvette window 49 is disposed within the optical path 21 and transmits the light beam passing through the sample to the calibrating light module 60, which then passes the light beam to the spectrometer module 100.

Figure 9:
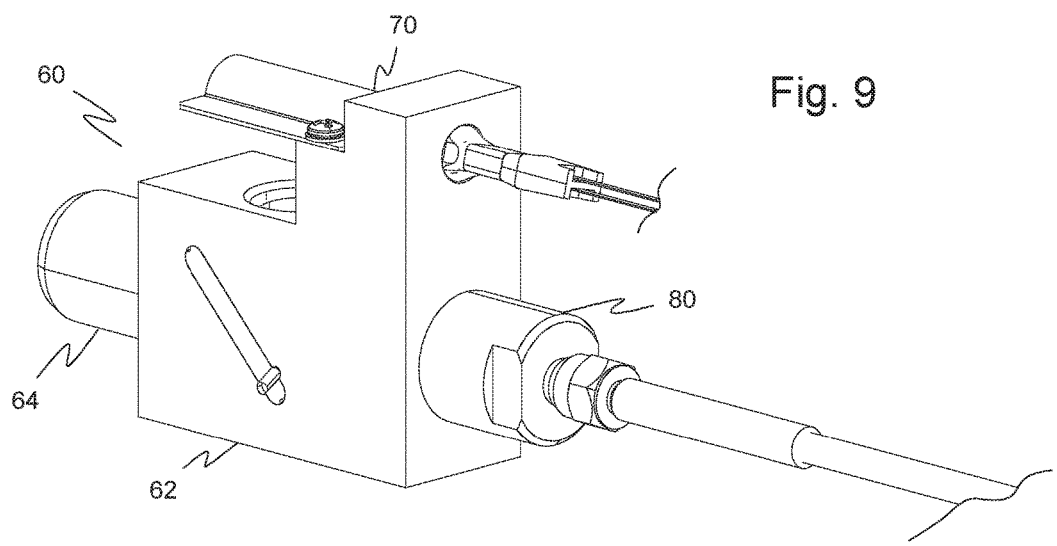
FIG. 9 is a perspective view of one embodiment of a calibrating light module of the optical-sample module of FIG. 1.

Turning now to FIG. 9, there is illustrated one embodiment of the calibrating light module 60. Calibrating light module 60 includes a calibrating module housing 62, a light beam receiving portion 64, a calibrating light portion 70, and an optic fiber portion 80 where calibrating module housing 62, light beam receiving portion 64 and optic fiber portion 80 are aligned with optical path 21. Calibrating light portion 70 is spaced from and transverse to optical path 21.

Figure 10:
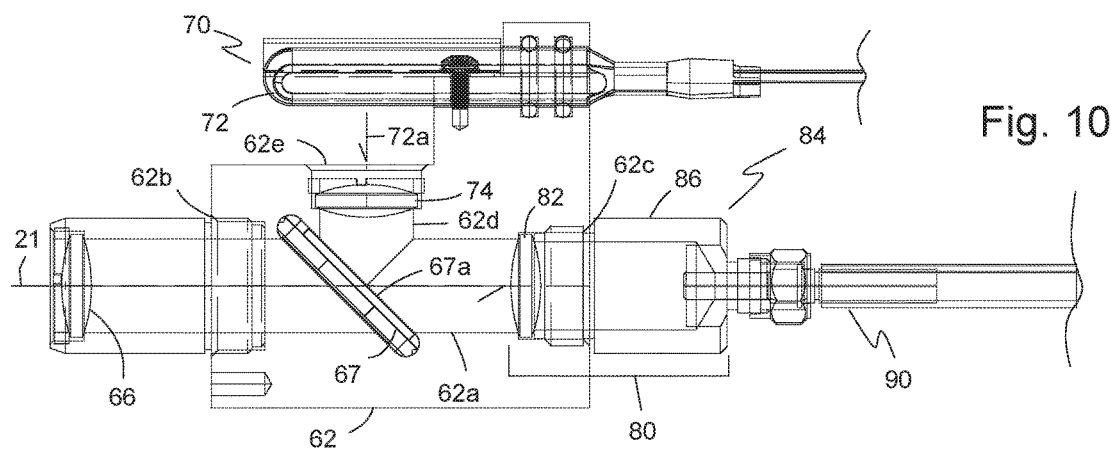
FIG. 10 is a side cross-sectional view of the calibrating light module of FIG. 8 showing a calibrating light source.

FIG. 10 is a cross-sectional, elevation view of calibrating light module 60. Calibrating module housing 62 includes a first tubular conduit 62a between a light beam input opening 62b and a light beam exit opening 62c as well as a second tubular conduit 62d that is transverse to and intersects with first tubular conduit 62a on one end and has a calibrating light beam opening 62e on an opposite end.

Light beam receiving portion 64 houses a collimating lens 66 that collimates light beam 28a received along optical path 21 from cuvette module 43 and directs light beam 28a into first tubular conduit 62a. Disposed within calibrating module housing 62 is beam splitter holder assembly 67 that is disposed transversely across first tubular conduit 62a. Beam splitter holder assembly 67 has an upward slanting surface 67a facing calibrating light beam opening 62e and light beam exit opening 62c within optical path 21. Beam splitter holder assembly 67 supports a second diffuser 68 and a beam splitter 69 (shown in FIG. 11) that is disposed downstream along optical path 21 from second diffuser 68 so that it is positioned to receive calibrating light beam 72a and direct it along optical path 21 and first tubular conduit 62a to light beam exit opening 62c.

Calibrating light portion 70 includes a calibrating light source 72 disposed adjacent but spaced from optical path 21 that is capable of directing a calibrating light beam 72a into calibrating module housing 62 through a calibrating light opening 62e transversely to optical path 21 toward beam splitter holder assembly 67. Within calibrating light portion 70, there is a collimating lens 74 that collimates calibrating light beam 72a before it is reflected by beam splitter assembly 67 toward light beam exit opening 62c.

Optic fiber portion 80 is located within optical path 21 at or in the vicinity of light beam exit opening 62c. Optic fiber portion 80 includes a focusing lens 82 and a optic fiber connector assembly 84 that includes a connector housing 86 adapted for receiving an optical fiber assembly 90. Optic fiber portion 80 is adapted to insure that light beam 28a is properly focused by focusing lens 82 into optical fiber assembly 90.

Figure 11:
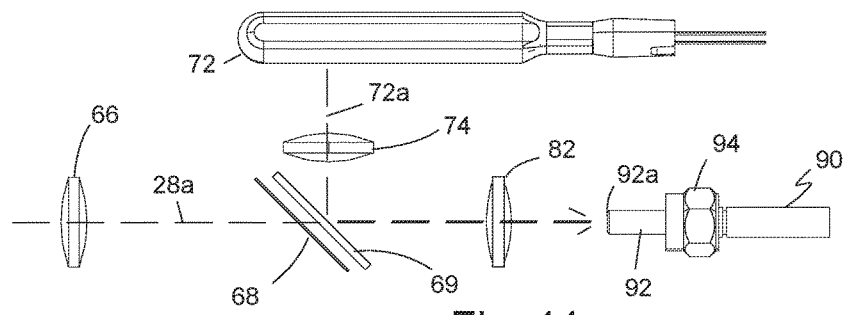
FIG. 11 is a simplified, side plan view of the calibrating light source of the calibrating light module of FIG. 9 showing a plurality of optical components.

FIG. 11 is a simplified illustration of FIG. 10 showing the positional relationship of the optical components 66, 68, 69, 74, 82 and light beams 28a, 72a as well as optical fiber assembly 90. As can be seen from FIG. 11, light beam 28a is received by collimating lens 66, transmitted through second diffuser 68 and beam splitter 69 to focusing lens 82 and into optical fiber assembly 90. As previously discussed, the importance of using a pair of diffusers (first diffuser 32 and second diffuser 68) with cuvette module 43 in between the pair of diffusers 32, 68 is that the spatial light distribution will appear the same for the blank scan and the whole blood sample scan. The use of diffusers 32, 68 in this arrangement removes the error effect caused by nonuniformity of the light source and/or variation in the spatial distribution changes of the incident light even if the overall intensity has not changed. Diffusers 32, 68 are chosen so that they diffuse a ray of incident light into the full acceptance cone of the optical component group 120 of the spectrometer module 100. This effectively scrambles the ray completely across the optical measuring field.

Calibrating light beam 72a when activated is received by collimating lens 74, transmitted to beam splitter 69 and directed to focusing lens 82 where it is focused into optical fiber assembly 90. Calibrating light beam 72a has specific wavelengths of light used for calibrating the wavelength scale of spectrometer module 100. One example of an acceptable calibrating light source 72 is a krypton (Kr) gas discharge lamp, which provides seven Kr line wavelengths in nanometers covering the range of 422 to 695 nm. Prism 131 of light dispersion component 130 has a nonlinear dispersion versus wavelength that requires a polynomial or other function of a higher order. The present invention uses a $5^{th}$ order polynomial to the pixel locations of the Kr line peaks to provide residual errors well below the absolute wavelength accuracy requirement of +/−0.03 nm.

Figure 12:
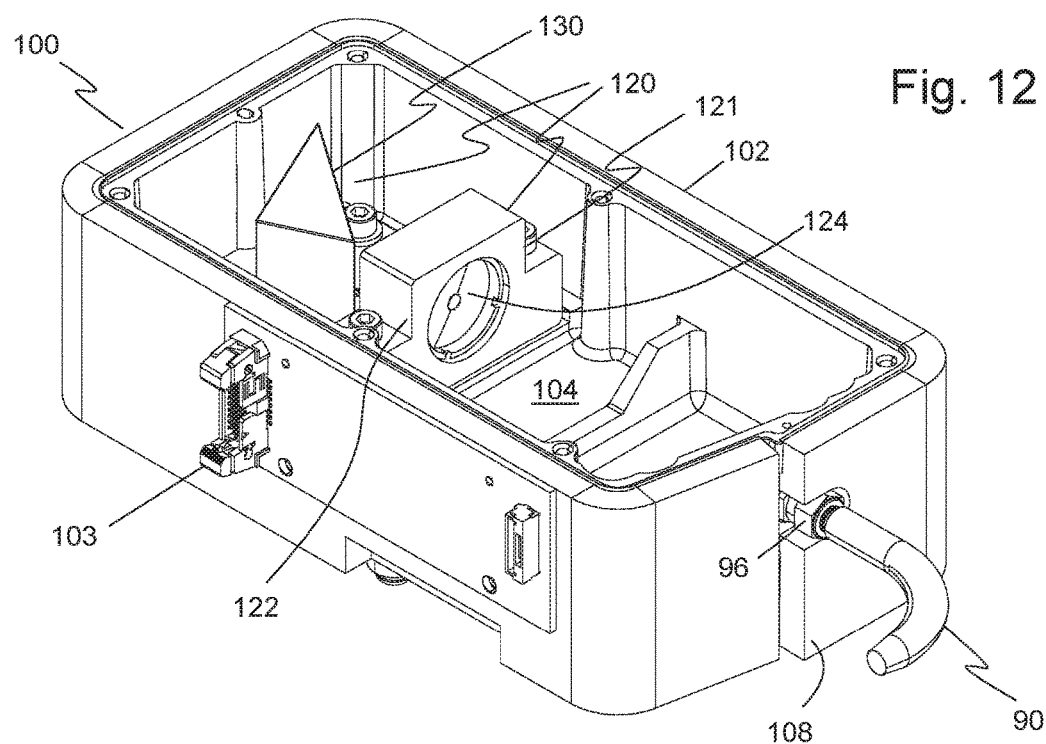
FIG. 12 is a front perspective view of one embodiment of a spectrometer module of FIG. 1 with a cover removed showing the internal components.

Optical fiber assembly 90 includes an optical fiber 92, a first optical fiber connector 94 and a second optical fiber connector 96 (shown in FIG. 12). First optical fiber connector 94 is secured to a light receiving end 92a of optical fiber 92 and directly and removably connects to connector housing 86 of optic fiber connector assembly 84. One embodiment of optical fiber 92 includes a 200 μm silica core fiber with a numerical aperture (NA) of 0.22.

Figure 13:
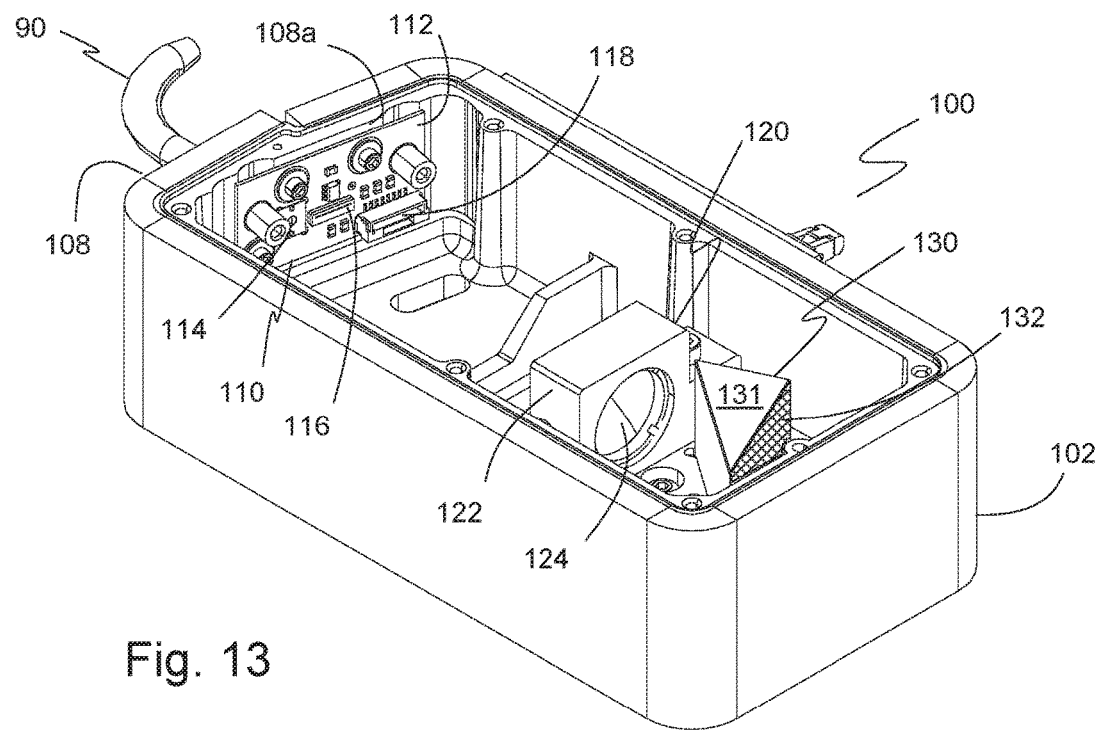
FIG. 13 is a rear perspective view of the spectrometer module of FIG. 12 showing an input light slit and adjacent light-array detector.

Turning now to FIGS. 12 and 13, there is illustrated one embodiment of spectrometer module 100. Spectrometer module 100 includes a spectrometer housing 102, a spectrometer base 104, a spectrometer cover 106 (shown in FIG. 1), an optical fiber housing end 108, and an electrical signal output coupler 103. Spectrometer module 100 has an outside envelope dimension of 11 cm×8 cm×2 cm and optionally includes thermal compensation structures discussed later. Within spectrometer housing 102 are contained the essential components of spectrometer module 100. These components include a light-receiving and converting assembly 110 and an optical component group 120. Optical component group 120 includes an achromatic lens assembly 121 and a light dispersing element 130. Light dispersing element 130 may be a prism 131 or a grating 136. Optical fiber assembly 90 is removably secured to optical fiber housing end 108 at light entrance port 109, which optical fiber assembly 90 transmits the light beams 28a, 72a to spectrometer module 100. As previously mentioned, light beam 28a represents the light transmitted from light-emitting module 22 through cuvette module 43 whereas light beam 72a is the calibrating light transmitted from calibrating light module 60, which is used to calibrate spectrometer module 100.

Achromatic lens assembly 121 includes a lens mount 122 and a spherical achromatic lens 124. Achromatic lens 124 receives light beams 28a, 72a, as the case may be, and directs the light beam to light dispersion element 130, which in this embodiment is prism 131. Prism 131 has a reflective coating 132 on an outside back surface. Prism 130 refracts light beam 28a and reflects the light back through achromatic lens 124.

Light-receiving and converting assembly 110 is securely mounted adjacent an inside surface 108a of optical fiber housing end 108. Light-receiving and converting assembly 110 includes a circuit board substrate 112 upon which is mounted a light input slit 114 that is aligned with light-emitting end 92b (not shown) of optical fiber 92. Adjacent input slit 114 is a light-array detector 116 that receives the refracted light from prism 131. Light-array detector 116 converts the refracted light to an electrical signal, which is output through output connector 118 to processor module 150. Providing light input slit 114 and light-array detector 116 adjacent each other on circuit board 112 has several advantages. This feature greatly simplifies the construction and improves the precision of spectrometer module 100. Other spectrometers place these items on separate planes, where they have separate mounting structures, and have to be adjusted independently. This feature of mounting the input slit and light-array detector adjacent each other on circuit board 112 eliminates the need to mount and position each structure (i.e. slit and detector) separately.

Figure 14:
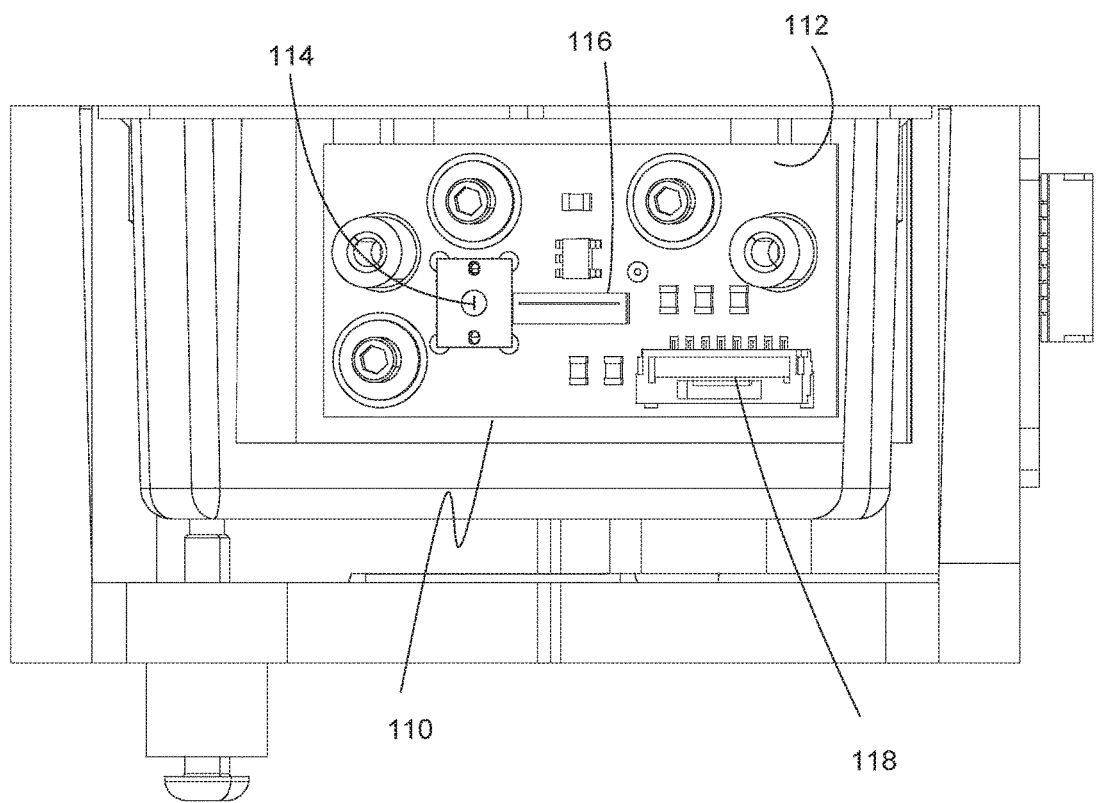
FIG. 14 is a rear cross-sectional view of the spectrometer module of FIG. 12 showing a single circuit board and the location of the input light slit and the light-array detector.

FIG. 14 is an enlarged view of light-receiving and converting assembly 110. Light input slit 114 is 15 µm wide by 1000 µm long that projects an optical fiber-slit image that is a rectangle approximately 15 µm wide by 200 µm high onto the light-array detector 116 (Hamamatsu S10226-10 is an example of a usable light array detector). Input slit 114 is applied directly onto the same circuit board substrate 112 as and in close proximity to light-array detector 116. Light-array detector 116 has a pixel height between about 100 to about 150 µm, which allows a one-to-one imaging of the 200 µm diameter optical fiber onto the detector. In this embodiment, input slit 114 is laser etched in a precise position relative to light-array detector 116 making alignment less labor intensive. Because input slit 114 and light-array detector 116 are only slightly off-axis relative to the center axis of the achromatic lens 124, there is minimal aberration and a one-to-one imaging on light-array detector 116 is possible so that no cylindrical focusing lens is required to shrink the optical fiber image (200 µm diameter fiber) to match the pixel height of light-array detector 116.

Figure 15:
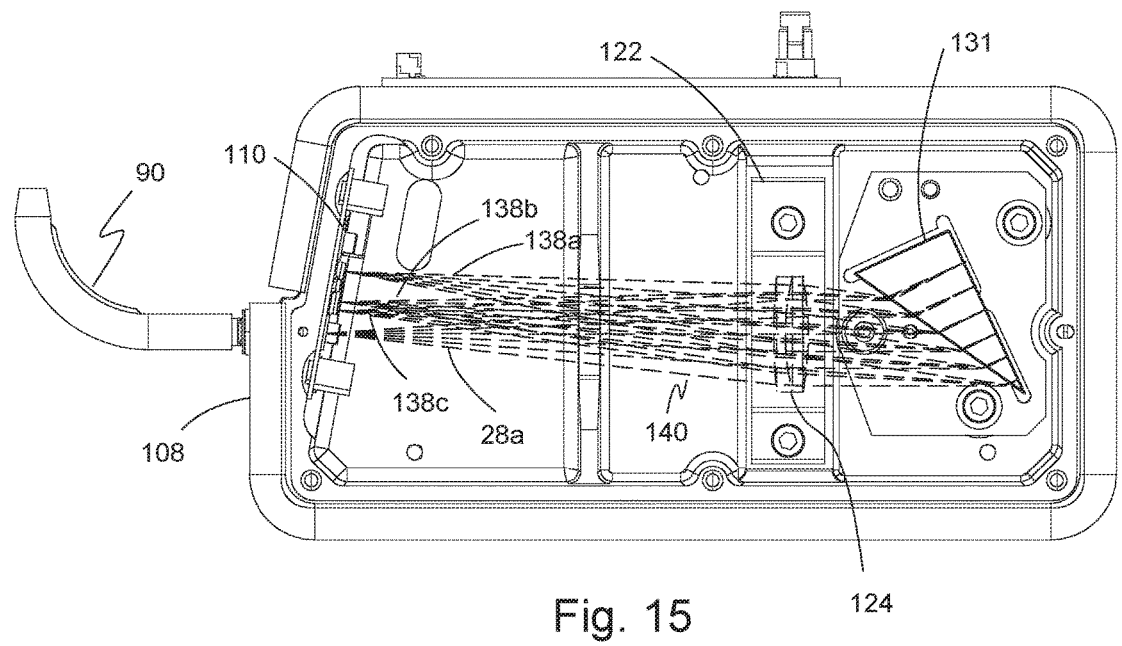
FIG. 15 is a top view of the spectrometer module of FIG. 12 showing the optical components with superimposed ray trace.

Turning now to FIG. 15, there is a top view of spectrometer module 100 of FIG. 13. Superimposed onto FIG. 15 is a ray trace diagram 140 of the light beam delivered to spectrometer module 100 by optical fiber 92. As shown, light beam 28a enters spectrometer module 100 through input slit 114 toward achromatic lens 124. Achromatic lens 124 is used off-axis; that is, the achromatic lens is slightly off-axis to the light beam 28a. Light beam 28a is transmitted by achromatic lens 124 to prism 131, where light beam 28a is refracted into a plurality of light beams 138a, 138b, 138c of different wavelengths as prisms are ought to do. The plurality of light beams 138a, 138b, 138c are reflected by prism 131 back through achromatic lens 124. Achromatic lens 124 is used off-axis in order to direct the plurality of refracted and reflected light beams 138a, 138b, 138c from prism 131 onto light-array detector 116.

Figure 16:
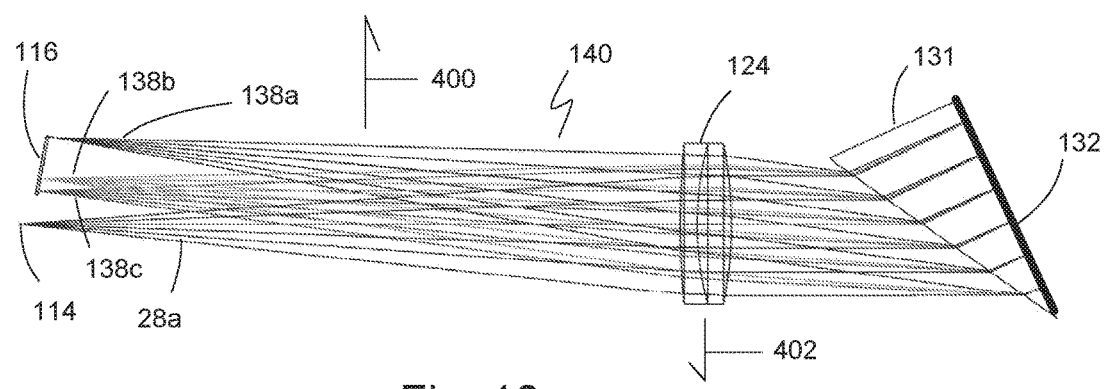
FIG. 16 is a ray trace showing the input light from the input light slit and a plurality of light beams refracted onto the light-array detector.

FIG. 16 is an enlarged view of ray trace diagram 140. Achromatic lens 124 is used off-axis relative to entering light beam 28a. By using achromatic lens 124 off-axis along with prism 131 having a reflective coating 132 on a base of prism 131, there is achieved a compact, simplified, minimal-component spectrometer module 100 capable of being used for measuring hemoglobin parameters and/or total bilirubin parameters in whole blood.

Figure 17A:
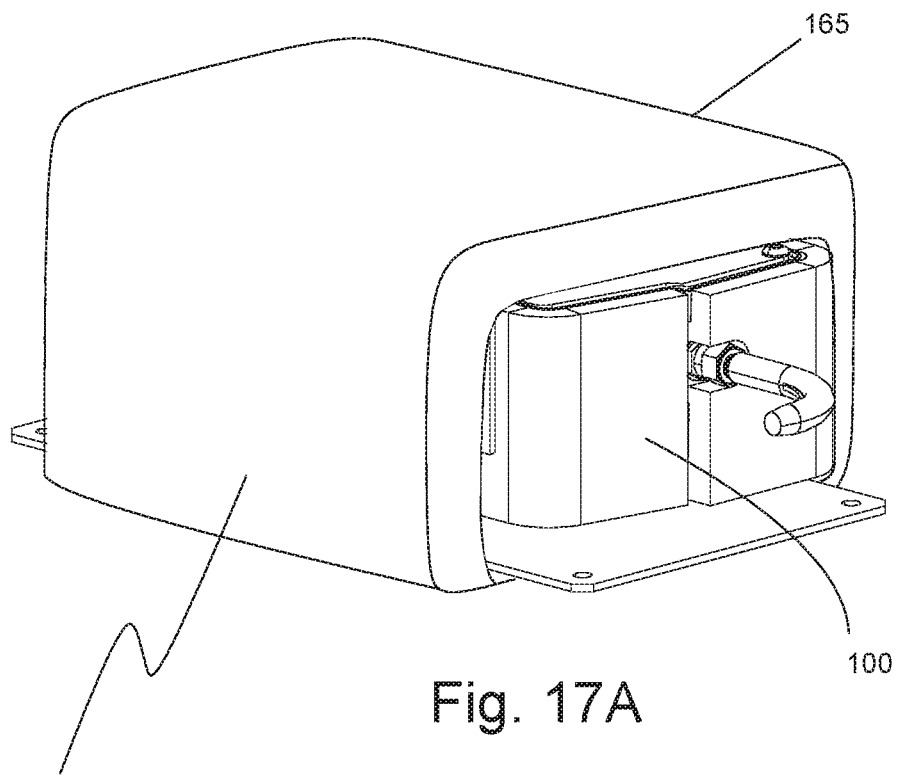
FIG. 17A is a perspective view of one embodiment of a thermal-compensating means for the spectrometer module showing insulation wrapped around the spectrometer module.
Figure 17B:
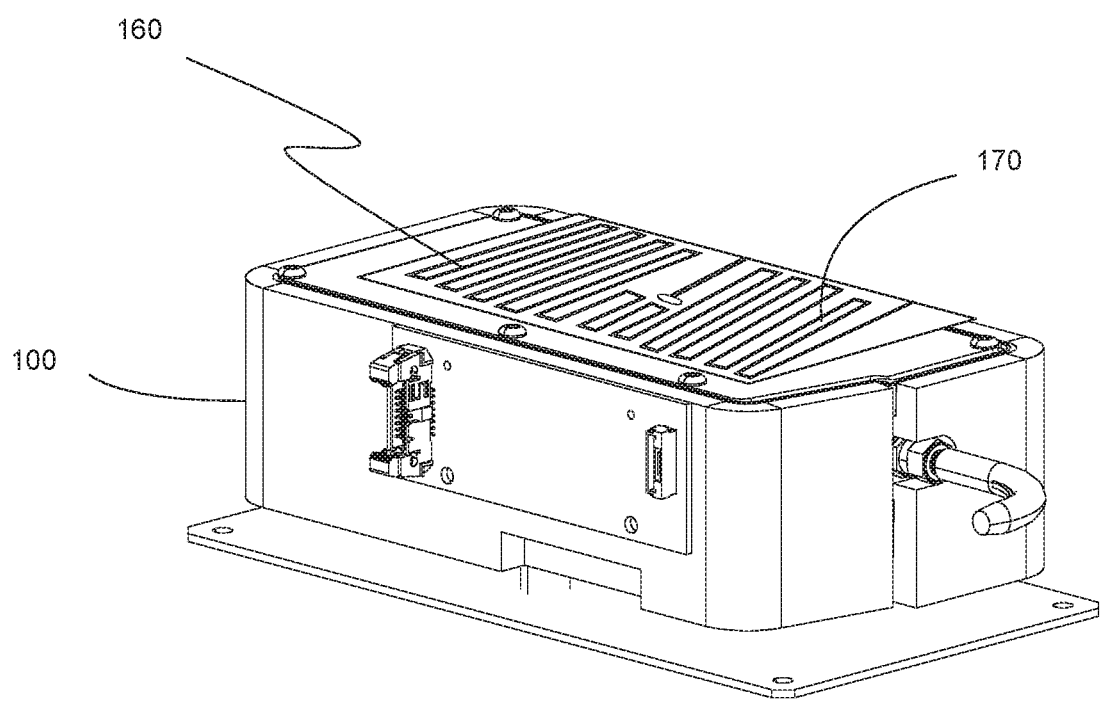
FIG. 17B is a perspective view of another embodiment of a thermal-compensating means for the spectrometer module showing a temperature controlling assembly.

A change in temperature has a greater effect on beam refraction angle when using a prism instead of a diffraction grating. In the present invention, a thermal-compensating means 160 is provided to compensate for a thermal shift in the incoming light beam caused by the light-dispersing element 130. A temperature change within spectrometer module 100 causes a thermally-induced movement of the slit image from input slit 114 on light-array detector 116 caused in turn by thermally-induced changes in refractive index of the dispersive prism 131. FIG. 16 shows the direction of movement of the image on light-array detector 116 for the thermal refractive index change in prism 131 with arrow 400. If the lens 124 is moved in the opposite direction over the same temperature interval as indicated by arrow 402, the slit image will be moved back to where it should be onto light-array detector 116. To prevent this shift, the thermal-compensating means 160 may be a simple as wrapping spectrometer module 100 with insulation to minimize temperature change within spectrometer module 100 from a temperature change occurring outside of spectrometer module 100 or to place spectrometer module 100 within a temperature controlled space. Another means is to include a temperature controller assembly 170 that includes at least a ribbon heater 172 attached to an inside surface or an outside surface of the spectrometer housing 102 and a temperature sensor 174 such as thermocouple or thermistor to measure the temperature of the spectrometer housing and a heater circuit to maintain a predefined constant temperature. FIGS. 17A and 17B illustrate these possibilities.

Figure 17C:
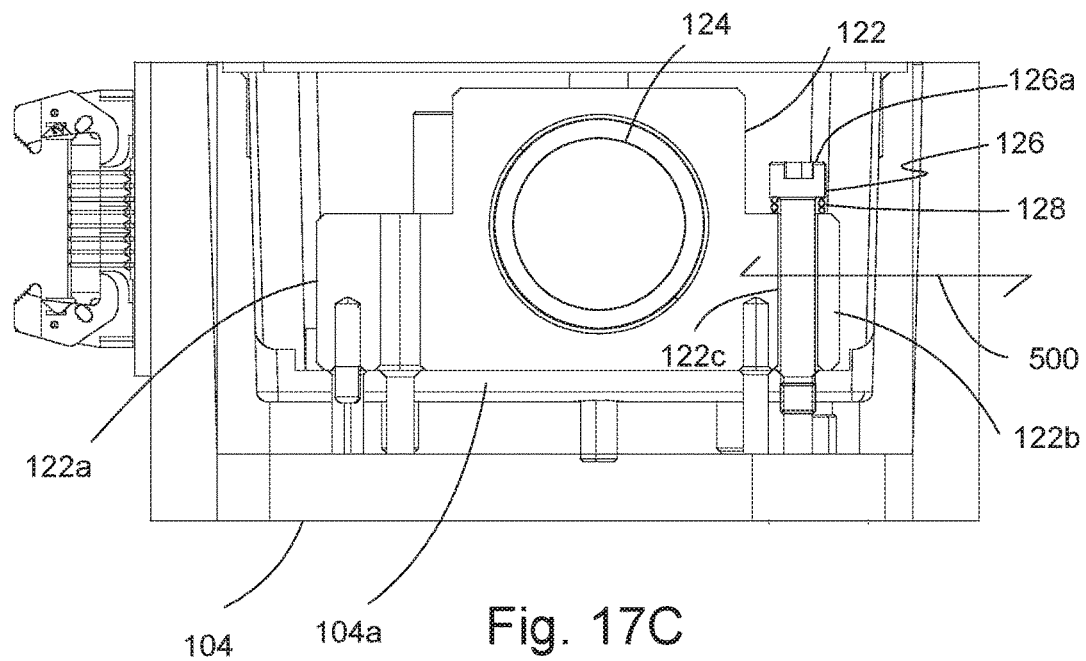
FIG. 17C is a cross-sectional view of one embodiment of a lens mount of the spectrometer module of FIG. 12 showing a temperature-compensating lens mount.

In one embodiment shown in FIG. 17C, achromatic lens mount 122 is a thermal-compensating lens mount. Thermal-compensating lens mount 122 has a fixed mount end 122a and an unfixed mount end 122b. Fixed mount end 122a is fixedly secured to spectrometer base 104 or a baseplate 104a that is securely attached to spectrometer base 104. Unfixed mount end 122b typically has a fastener 126 that extends through a lens mount slot 122c of lens mount 122 and into spectrometer base 104 or baseplate 104a. Between a head 126a of fastener 126 and lens mount 122 is a hold-down spring 128. There is sufficient spacing between lens mount slot 122c and fastener 126 to permit expansion/contraction of lens mount 122 caused by a temperature change. The coefficient of expansion of lens mount 122 is greater than the coefficient of expansion of spectrometer base 104 and/or baseplate 104a so that unfixed mount end 122b permits thermal expansion and contraction of thermal-compensating lens mount 122 in a direction shown by arrow 500, which is linear and transverse to the light beam from input slit 114. This structure allows achromatic lens 124 to slide relative to other components mounted on baseplate 104a and/or spectrometer base 104. Thermal-compensated lens mount 122 ensures that the plurality of light beams 138a, 138b, 138c will always impinge with sufficient intensity onto light-array detector 116 without affecting the electrical signal generated by light-array detector 116 notwithstanding a temperature change within spectrometer housing 102. One such material that meets the requirement that lens mount 122 have a greater coefficient of expansion than spectrometer base 104 and/or baseplate 104a (as the case may be) is a plastic that is a modified polyphenylene ether (PPE) resin consisting of amorphous blends of polyphenylene oxide (PPO) polyphenylene ether (PPE) resin and polystyrene sold under the trademark NORYL®.

Figure 18:
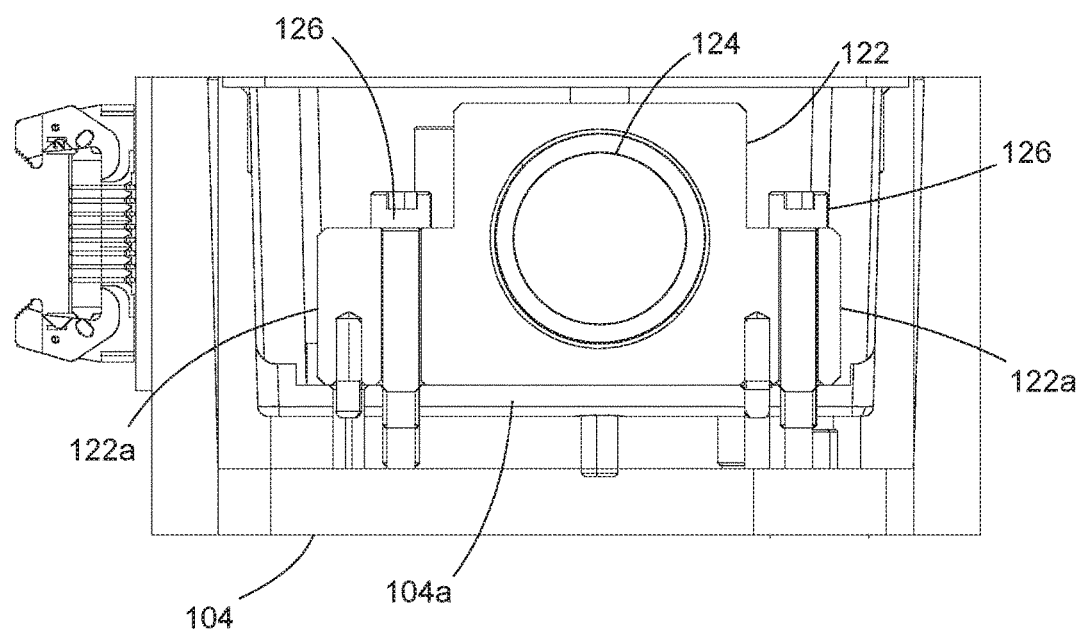
FIG. 18 is a cross-sectional view of one embodiment of a lens mount of the spectrometer module of FIG. 12 showing a fixed lens mount.

FIG. 18 illustrates an alternative embodiment of lens mount 122. In this embodiment, lens mount 122 has two fixed mount ends 122a, where each end 122a is secured to baseplate 104a and/or spectrometer base 104 by fastener 126. Because both ends 122a of lens mount 122 are fixed, any temperature change within spectrometer module 100 will affect angle of the plurality of light beams 138a, 138b, 138c and where they impinge on light-array detector 116. As previously disclosed regarding the slit image and the length of the light-array detector 116, a temperature change of greater than 0.5° C. will cause the intensity of one of the light beams to not impinge completely on the light-array detector thereby causing an inaccurate reading. To nullify this potential effect, spectrometer module 100 is equipped with a temperature controller assembly (not shown) so that prism 131 and achromatic lens assembly 121 remain at a constant temperature. Although there are several methods available for maintaining the inside of spectrometer module 100 at a constant temperature, one example of such a temperature controller assembly to accomplish this is a ribbon heater with a thermistor (not shown) adhesively attached to the inside or outside of spectrometer module 100, which ribbon heater is controlled by an electronic regulation circuit (not shown). Optionally, spectrometer module 100 may also be insulated either inside or outside or both to more easily maintain a given temperature and protect against changes in temperature in the vicinity surrounding spectrometer module 100. Other mechanisms include placement of spectrometer module 100 within a temperature controlled environment.

Learning Data:

A data set of about 180 blood samples from approximately 15 different individuals was developed. The blood samples were manipulated using sodium nitrite to raise MetHb values, and using CO gas to raise COHb values. Plasma was removed from or added to samples to change the tHb level. Bilirubin spiking solution was added to vary the tBil level. A tonometer was used to manipulate the oxygen level. The blood samples were manipulated to cover a large range of analyte values. The blood samples were then measured on a reference lysing pHOx Ultra analyzer equipped with COOx analyzer and analysis software. The whole blood spectra were gathered on a pHOx Ultra analyzer equipped with the high-angle collection optics and other modifications of the present invention, as described earlier, with the lyse supply line completely disconnected and the whole blood samples running directly into the cuvette assembly 40 without lyse or any other dilution. Both analyzers were equipped with Zeonex windows in the respective cuvettes. This data set has been turned into a Matlab cell array file for use with Matlab scripts.

Prediction Model:

The next step in the calculation is to create a prediction model. Three models were developed for the analysis: one for the COOx parameters tHb and COHb, a second for HHb and MetHb, and a third for tBil. The quantity for O2Hb was determined by subtracting COHb, HHb, and MetHb from 100%. The X-data array was constructed from terms created from the measured absorbance at the wavelengths between 462-650 nm, 1 nm spacing. The tBil model was developed using the same set of data as the COOx model, except that samples with MetHb values greater than or equal to 20% were left out of the model. For each model, five Y-predictive values were assigned (O2Hb, HHb, COHb, MetHb, tBil) with tHb determined by adding the results for O2Hb, HHb, COHb, and MetHb. The number of Y-orthogonal values needed was determined by manual optimization of the correlation residual of the mapping function blood predictions with the reference analyzer values.

Using an initial calibration data set, the calibration sequence of a machine learning algorithm establishes a relationship between a matrix of known sample characteristics (the Y matrix) and a matrix of measured absorbance values at several wavelengths and potentially other measured values based on absorbance versus wavelength (the X matrix). Once this relationship is established, it is used by the analyzer to predict the unknown Y values from new measurements of X on whole blood samples.

Table 1 summarizes the settings and inputs used for the optimized models. The X-data consists of the absorbance and other terms based on absorbance vs. wavelength. In the process of optimizing the model, absorbance derivatives vs. wavelength were added. Models for analytes more sensitive to nonlinear scatter effects were built up with square root terms of the absorbance and its derivative. The model for analytes more affected by scatter had a correction term proportional to the fourth power of the wavelength. The X-vector row has one value for each wavelength for each of the three absorbance-based terms f, g, and h shown in the table for each model.

TABLE 1

Parameters used to construct algorithm models (KOPLS method).

| Model | Y-predictive components | Y-orthogonal components | X data structure (from absorbance vs. wavelength) | Kernel polynomial exponent |
|---|---|---|---|---|
| tHb, COHb | 5 | 4 | $f(\lambda) = \sqrt{\frac{dA(\lambda)}{d\lambda}}$, $g(\lambda) = \frac{dA(\lambda)}{d\lambda}$, $h(\lambda) = \sqrt{A(\lambda)}$ | 0.5 |
| HHb, MetHb | 5 | 4 | $f(\lambda) = \frac{dA(\lambda)}{d\lambda}$, $g(\lambda) = A(\lambda) \cdot \left(\frac{\lambda}{650 \text{ nm}}\right)^4$, $h(\lambda) = A(\lambda)$ | 1.0 |
| tBil | 5 | 16 | $f(\lambda) = \sqrt{\frac{dA(\lambda)}{d\lambda}}$, $g(\lambda) = \sqrt{A(\lambda)}$, $h(\lambda) = A(\lambda)$ | 1.0 |

The calibration set Y matrix is built up as follows from the known values of the calibration sample set of n lysed blood samples:

$$Y = \begin{bmatrix} tHb_1 & COHb_1 & HHHb_1 & MetHb_1 & tBil_1 \\ tHb_2 & COHb_2 & HHHb_2 & MetHb_2 & tBil_2 \\ \ldots & \ldots & \ldots & \ldots & \ldots \\ tHb_n & COHb_n & HHHb_n & MetHb_n & tBil_n \end{bmatrix}$$

where tHb is the total hemoglobin value of the lysed blood sample,

COHb is the carboxyhemoblogin value of the lysed blood sample,

HHb is the deoxyhemoglobin value of the lysed blood sample,

MetHb is the methemoglobin value of the lysed blood sample, and tBil is the total bilirubin value of the lysed blood sample.

The X matrix is structured as follows:

$$X = \begin{bmatrix} f_1(\lambda_1), \ldots f_1(\lambda_n), & g_1(\lambda_1), \ldots g_1(\lambda_n), & h_1(\lambda_1), \ldots h_1(\lambda_n) \\ \vdots & \ddots & \vdots \\ f_n(\lambda_1), \ldots f_n(\lambda_n), & g_n(\lambda_1), \ldots g_n(\lambda_n), & h_n(\lambda_1), \ldots h_n(\lambda_n) \end{bmatrix}$$

where: f, g, h are the absorbance-based functions listed in Table 1 versus wavelength, respectively.

The matrix X includes contributions from absorbance at the various wavelengths. The scope of the invention includes optionally adding other measurements to the calculation to reduce interferent effects.

Once these matrices are formed, they are used as the calibration set and the mapping function is computed according to the procedures particular to the machine learning algorithm chosen.

As described previously, conventional partial least squares, linear regression, linear algebra, neural networks, multivariate adaptive regression splines, projection to latent structures, kernel-based orthogonal projection to latent structures, or other machine learning mathematics is used with results obtained from the calibration set of data to determine the empirical relationship (or mapping function) between the absorbance values and the hemoglobin parameters. Typically, a mathematics package is used to generate the results where the package generally has options to select one of the machine learning mathematics known to those skilled in the art. Various mathematics packages exist and include, but are not limited to, Matlab by MatWorks of Natick, Mass., "R" by R Project for Statistical Computing available over the Internet at www.r-project.org, Python from Python Software Foundation and available over the Internet at www.python.org in combination with Orange data mining software from Orange Bioinformatics available over the Internet at orange.biolab.si, to name a few.

It will be shown that the method of Kernel-Based Orthogonal Projection to Latent Structures (KOPLS) may be used as one type of machine learning algorithm to generate the mapping function. An explanation and description of KOPLS is best exemplified by the following references: Johan Trygg and Svante Wold. "*Orthogonal projections to latent structures (O-PLS)*." J. Chemometrics 2002; 16: 119-128; Mattias Rantalainen et al. "*Kernel-based orthogonal projections to latent structures (K-OPLS)*." J. Chemometrics 2007; 21: 376-385; and Max Bylesjö et al. "*K-OPLS package: Kernel-based orthogonal projections to latent structures for prediction and interpretation in feature space*." BMC Bioinformatics 2008, 9:106, which references are incorporated herein by reference. The kernel-based mathematics is useful in handling non-linear behavior in systems by using a kernel function to map the original data to a higher order space. Although any of the previously described machine learning mathematics may be used to enable one of ordinary skill in the art to practice the present invention, KOPLS has an additional advantage over other calculations such as, for example, conventional partial least squares because it can not only establish a relationship between quantified variations and analyte values to be determined, but can also remove unquantitated yet consistently present variation in the original data. These unquantitated variations might be due to analyzer and/or blood effects such as scatter losses and other interfering phenomena that are not explicitly measured. By extracting these unquantitated variations from the data, the method leaves behind in the data the information used to predict the measured values.

Using an initial training data set, the KOPLS model establishes a relationship (mapping function) between the matrix of known sample characteristics (the H matrix), and a matrix of measured absorbance values at several wavelengths and potentially other measured values based on absorbance versus wavelength (the X matrix) as processed through a kernel function as specified by the KOPLS method. Once the KOPLS coefficients of this relationship are established, they are used with the kernel function by the analyzer to predict the unknown hemoglobin parameter values from new measurements of absorbance on samples.

The kernel function used in this example is a simple linear kernel function described in the Mattias Rantalainen et al. reference listed above and represented by the following equation:

$$\kappa(X,X) = \langle X, X \rangle$$

where the matrix of measured values X is put into the kernel function and subjected to further processing as specified in the cited KOPLS references above (incorporated by reference) for creating the KOPLS training coefficients.

Once the set of training coefficients, or mapping function, is established, it is used to predict the hemoglobin parameter values and/or total bilirubin parameter values of a blood sample from future measurements. A single-row X matrix is created from the new measurements, then the value from this single-row X matrix is put through the kernel and mapping functions to produce the hemoglobin parameter values and/or total bilirubin parameter values according to the procedures necessary for the mapping function used according to the KOPLS procedures described in detail in the KOPLS references disclosed previously.

The data collected from the blood samples described above were put through the KOPLS method in a cross-validation process. Cross-validation is a process for using a data set to test a method. Several data rows are set aside and the rest are used to create a mapping function. The set-aside values are then used as "new" measurements and their Y matrix values calculated. This process is repeated by setting aside other measured values and computing another mapping function. By plotting the known values of the blood data vs. the calculated, the effectiveness of the method may be ascertained by inspecting the plot.

Turning now to FIGS. 18-23, there are illustrated graphical plots of the correlation results comparing the various hemoglobin parameters of lysed blood to whole blood using the KOPLS method. The blood samples were manipulated to cover a large range of analyte values. The technique of n-fold cross-validation using 60 folds was used to test the data. In this technique, the data set is divided into n=60 separate sets, and the model is made from n−1 of the sets, with the remaining set predicted using the model. The process is repeated 60 times for each group. Every data point is thus predicted using a model made from most of the other data points, without being included in the model.

Figure 19:
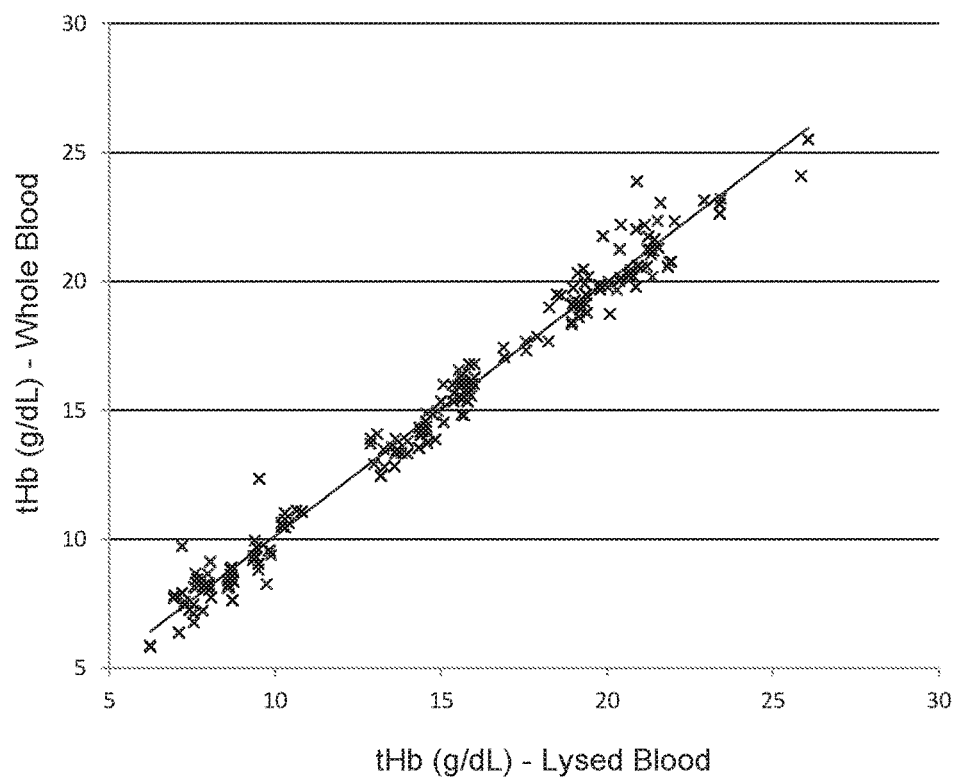
FIG. 19 is a graphic illustration showing the correlation results of the COOx analyzer subsystem of the present invention for total hemoglobin using a K-OPLS mapping function and method.

FIG. 19 shows the correlation results for tHb using the K-OPLS method. The horizontal axis has units representing the total hemoglobin in grams per deciliter of lysed blood. The vertical axis has units representing total hemoglobin in grams per deciliter of whole blood. As can be seen from the plot, the method of determining tHb of a whole blood sample has a correlation of greater than 99%.

Figure 20:
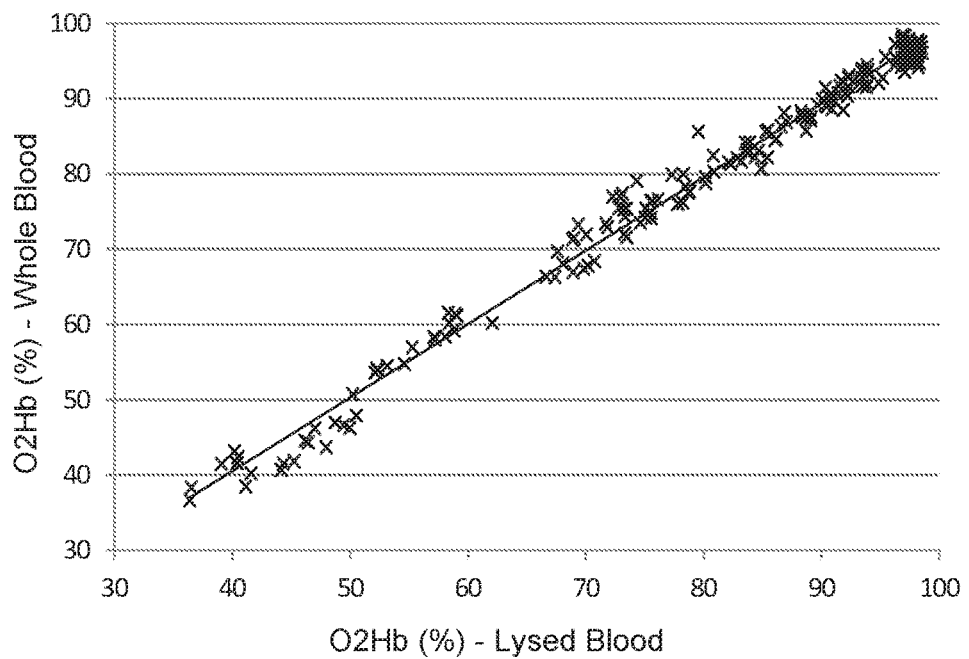
FIG. 20 is a graphic illustration showing the correlation results of the COOx analyzer subsystem of the present invention for oxyhemoglobin using a K-OPLS mapping function and method.

FIG. 20 shows the correlation results for O2Hb using the K-OPLS method. The horizontal axis has units representing the percent oxyhemoglobin of lysed blood. The vertical axis has unit representing percent oxyhemoglobin of whole blood. As seen from the plot, the method of determining O2Hb of a whole blood sample has a correlation of greater than 99%.

Figure 21:
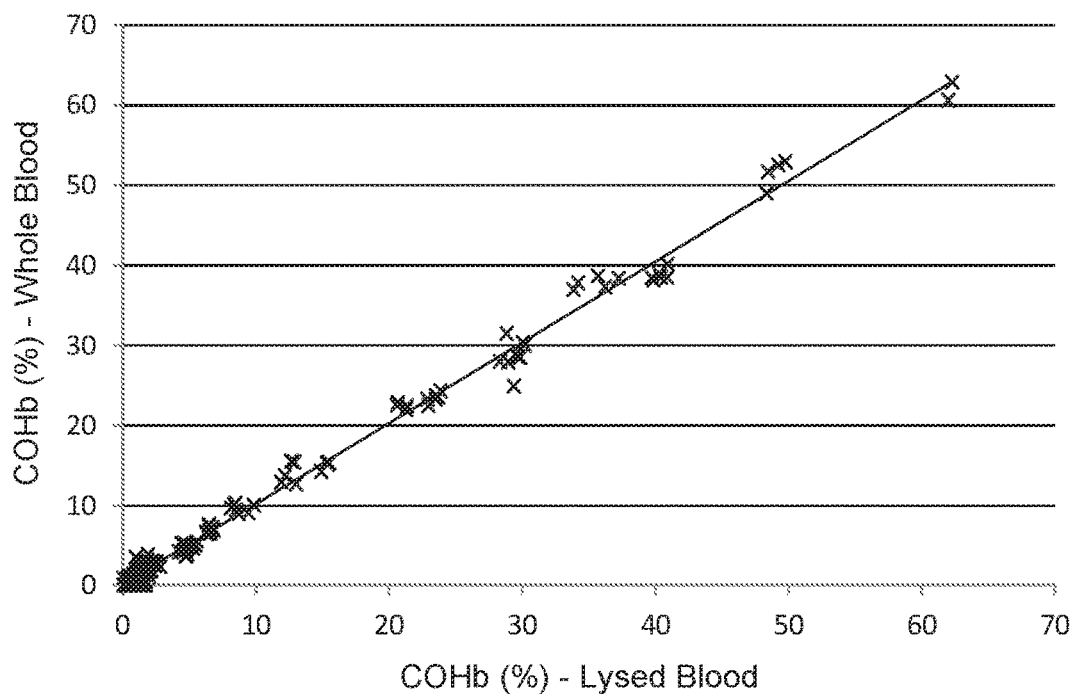
FIG. 21 is a graphic illustration showing the correlation results of the COOx analyzer subsystem of the present invention for carboxyhemoglobin using a K-OPLS mapping function and method.

FIG. 21 shows the correlation results for carboxyhemoglobin using the K-OPLS method. The horizontal axis has units representing the percent carboxyhemoglobin of lysed blood. The vertical axis has unit representing percent carboxyhemoglobin of whole blood. As seen from the plot, the method of determining COHb of a whole blood sample has a correlation of greater than 99%.

Figure 22:
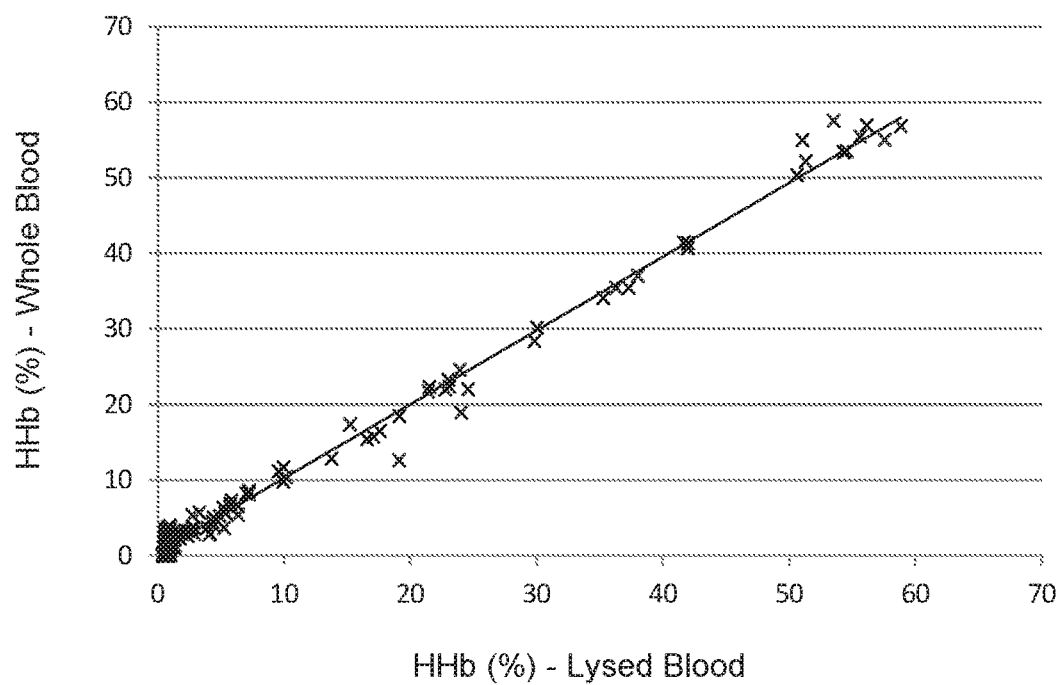
FIG. 22 is a graphic illustration showing the correlation results of the COOx analyzer subsystem of the present invention for deoxyhemoglobin using a K-OPLS mapping function and method.

FIG. 22 shows the correlation results for deoxyhemoglobin using the K-OPLS method. The horizontal axis has units representing the percent deoxyhemoglobin of lysed blood. The vertical axis has unit representing percent deoxyhemoglobin of whole blood. As seen from the plot, the method of determining HHb of a whole blood sample has a correlation of greater than 99%.

Figure 23:
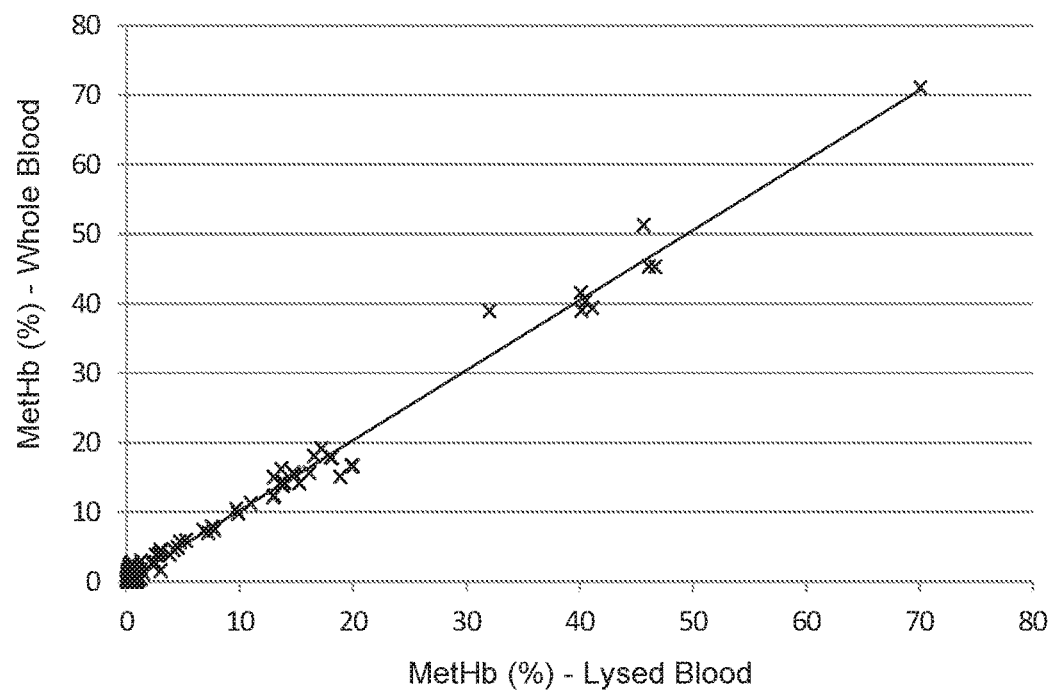
FIG. 23 is a graphic illustration showing the correlation results of the COOx analyzer subsystem of the present invention for methemoglobin using a K-OPLS mapping function and method.

FIG. 23 shows the correlation results for methemoglobin using the K-OPLS method. The horizontal axis has units representing the percent methemoglobin of lysed blood. The vertical axis has unit representing percent methemoglobin of whole blood. As seen from the plot, the method of determining MetHb of a whole blood sample has a correlation of greater than 99%.

Figure 24:
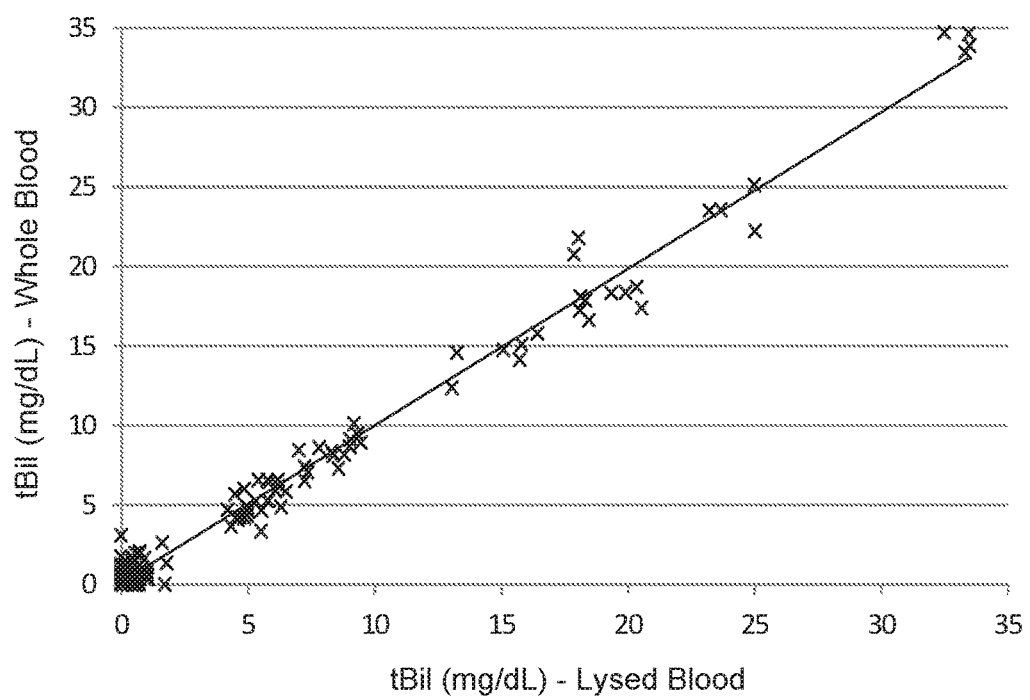
FIG. 24 is a graphic illustration showing the correlation results of the COOx analyzer subsystem of the present invention for total bilirubin using a K-OPLS mapping function and method.

FIG. 24 shows the correlation results for tBil using the K-OPLS method. The horizontal axis has units representing the total bilirubin in milligrams per deciliter of lysed blood. The vertical axis has units representing total bilirubin in milligrams per deciliter of whole blood. As can be seen from the plot, the method of determining tBil of a whole blood sample has a correlation of greater than 99%.

A method of making a whole blood measurement using the COOx analyzer subsystem 10 of the present invention will now be described. An absorbance scan is measured by first recording a transmitted light intensity scan with cuvette module 43 filled with a transparent fluid such as water or analyzer flush solution otherwise known as the 'blank' scan. Then a transmitted light intensity scan with cuvette module 43 filled with the whole blood sample is recorded. After corrections for spectrometer dark response and detector linearity, the spectral absorbance is the negative of the logarithm to the base ten of the ratio of the whole blood scan to the transparent fluid scan computed at each wavelength in the measurement range.

More specifically, a depiction of the components of a COOx analyzer subsystem is shown in FIGS. 1-18. This subsystem embodiment measures the optical absorbance of liquids introduced into cuvette module 43. The light used to perform the absorbance measurement originates from LED light source 28, is collected and transmitted by collimating lens 30, passes through first diffuser 32, circular polarizer 34, focusing lens 36, and optional protective window 38 before reaching cuvette module 43. Critical to an absolute absorbance measurement is knowledge of the cuvette path length. The cuvette path length is pre-measured for each individual cuvette module 43 and programmed into an electronic chip 48c on cuvette module 43. The path length information is read/retrieved by data processor module 130 of the analyzer whenever required.

After passing through cuvette module 43, the light is collected by lens 66, collimated and sent through second diffuser 68 and beam splitter 69. The purpose of beam splitter 69 is to allow light from calibrating light source 72 (for example, a krypton gas-discharge lamp), collimated by lens 74, to enter optical path 21. Calibrating light source 72 provides light at a few known wavelengths, which are used to periodically recalibrate the wavelength scale of spectrometer module 100. After passing through the beam splitter 69, the light is focused by lens 82 onto an optical fiber 92. The optical fiber 92 guides the light to input slit 114 of spectrometer module 100. The light passes through an achromatic lens 124, goes through light dispersion element 130 with a reflective back 132. The light is wavelength-dispersed by passing through light dispersion element 130 such as, for example, prism 130 then makes a return pass through the lens 124, which re-focuses the light onto the pixels of light-array detector 116. Light-array detector 116 converts the light energy into an electrical signal which represents the spectral intensity of the light. The electrical signal is sent to data processor module 150 for further processing and display of the final results to the user. Light-receiving and converting assembly 110 is a single board that holds input slit 114 and light-array detector 116 in close proximity as an integrated unit.

Input slit 114 is applied directly onto the same circuit board substrate 112 as and in close proximity to light-array detector 116. Other prior art spectrometers place these components on separate planes where they have separate mounting structures needing independent adjustment and alignment. The mounting scheme of the present invention has several advantages that lower the cost and size of spectrometer module 100: 1) cost of separate mounting structures is avoided, 2) input slit 114 can be laser etched in a precise position relative to light-array detector 116 making alignment less labor intensive, 3) inexpensive spherical surface optics can be used in the optical system since the image of the slit on the detector is only slightly off-axis from the center axis of the optical system, minimizing aberration, and 4) a single alignment procedure for a unified slit and detector assembly replaces alignment procedures for two separate assemblies.

It is important to note that first diffuser 32 and second diffuser 68 are positioned before and after cuvette module 43, respectively. Optical absorbance measurement of a diffuse sample presents a unique problem. The diffuse transmittance of the sample scrambles the initial spatial light distribution of the measurement system caused by the non-uniformity typical of light sources. Thus, the spatial light distribution of the 'blank' scan can be quite different from the whole blood sample scan. Since optical detectors have response that varies spatially, the response can vary due to spatial distribution changes of the incident light, even if the overall intensity has not changed. An absorbance scan which is based on the ratio of the sample scan to the blank scan will have a significant absorbance component due to this effect in addition to the absorbance due to the sample alone. This results in a significant measurement error of the sample absorbance that is intolerable for cooximetry.

The advantage of placing cuvette module 43 between first and second diffusers 32, 68 is that the spatial light distribution will appear the same for the blank and sample scans, removing this error effect. Diffusers 32, 68 are specially chosen so that they diffuse a ray of incident light into the full acceptance cone of the optical system, but not more so, so that as much light throughput as possible may be preserved while scrambling the light ray completely across the field.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. A method of measuring hemoglobin parameters in a whole blood sample using optical absorbance, the method comprising:
measuring and recording a transmitted light intensity scan over a plurality of wavelengths in a measurement range by transmitting light through a cuvette module having an optical path with a known optical path length therethrough wherein the cuvette module is filled with a transparent fluid;
measuring and recording a transmitted light intensity scan over the plurality of wavelengths of the measurement range by transmitting light through the cuvette module a second time having the optical path with the known optical path length therethrough wherein the cuvette module is filled with a whole blood sample, wherein each measuring and recording step of the transparent fluid and the whole blood sample includes diffusing and circularly polarizing the transmitted light before transmitting the transmitted light through the cuvette module and then diffusing the transmitted light emitting from the cuvette module before determining a spectral absorbance at each wavelength of the plurality of wavelengths of the measurement range determining the spectral absorbance at each wavelength of the plurality of wavelengths of the measurement range based on a ratio of the transmitted light intensity scan of the whole blood sample to the transmitted light intensity scan of the transparent fluid using a spectrometer; and correlating the spectral absorbance at each wavelength of the plurality of wavelengths of the measurement range to hemoglobin parameter values and/or bilirubin parameter values of the blood sample using a computational mapping function.

2. The method of claim 1 further comprising controlling a temperature-caused drift of the transmitted light within the spectrometer by one or more of insulating the spectrometer, controlled heating of the spectrometer or incorporating a thermal-compensating lens mount within the spectrometer.

3. The method of claim 2 wherein incorporating 5 the thermal-compensating lens mount includes moving linearly and transversely the thermal-compensating lens mount relative to an optical path of light from a light input slit based on a coefficient of expansion of the temperature compensating lens mount to maintain a position of the transmitted light from a light-dispersing element onto a light-array detector.

4. The method of claim 1 further comprising selecting the cuvette module having an electronic chip disposed thereon, measuring the optical path length of the cuvette module and storing the optical path length electronically in the electronic chip of the cuvette module.

5. The method of claim 1 wherein the correlating step further includes selecting a computational mapping function that is a kernel-based orthogonal projection to latent structures function.

6. The method of claim 5 wherein the correlating step includes mapping the hemoglobin parameters of total hemoglobin, carboxyhemoglobin, deoxyhemoglobin, and methemoglobin to respective known levels in blood.

7. The method of claim 5 wherein the correlating step includes mapping a total bilirubin value to known total bilirubin values in blood.

8. The method of claim 1 wherein the determining step includes using a spectrometer having a light input slit and a light-array detector mounted adjacent each other on a single substrate, a thermal-compensating lens disposed in a lens mount having a fixed end and an unfixed end whereby the lens mount linearly and transversely shifts the lens across the optical path when a temperature change occurs within the spectrometer to thereby maintain light from the input slit that is separated into a plurality of light beams by a prism or a grating focused onto the light-array detector without affecting an electrical signal generated by the light-array detector by the plurality of light beams.

9. The method of claim 8 further comprising calibrating the spectrometer by guiding a calibrating light from a calibrating-light module into the spectrometer wherein the calibrating light has specific wavelengths of light for calibrating the wavelength scale of the spectrometer.

* * * * *